(12) United States Patent
Lin et al.

(10) Patent No.: US 10,370,658 B2
(45) Date of Patent: Aug. 6, 2019

(54) COMPOSITION AND METHOD OF USING MIR-302 PRECURSORS AS ANTI-CANCER DRUGS FOR TREATING HUMAN LUNG CANCER

(71) Applicants: Shi-Lung Lin, Arcadia, CA (US);
Donald C. Chang, Cerritos, CA (US);
David T S Wu, Arcadia, CA (US);
Hsuan-Hsuan Lu, Taipei (TW)

(72) Inventors: Shi-Lung Lin, Arcadia, CA (US);
Donald C. Chang, Cerritos, CA (US);
David T S Wu, Arcadia, CA (US);
Hsuan-Hsuan Lu, Taipei (TW)

( * ) Notice: Subject to any disclaimer, the term of this patent is extended or adjusted under 35 U.S.C. 154(b) by 52 days.

(21) Appl. No.: 15/442,557

(22) Filed: Feb. 24, 2017

(65) Prior Publication Data

US 2017/0175118 A1 Jun. 22, 2017

Related U.S. Application Data

(60) Continuation-in-part of application No. 15/167,226, filed on May 27, 2016, now Pat. No. 9,879,263, and a continuation-in-part of application No. 15/167,219, filed on May 27, 2016, now abandoned, said application No. 15/167,226 is a continuation-in-part of application No. 14/527,439, filed on Oct. 29, 2014, now Pat. No. 9,637,747, and a continuation-in-part of application No. 14/502,608, filed on Sep. 30, 2014, now Pat. No. 9,783,811, and a continuation-in-part of application No. 14/142,512, filed on Dec. 27, 2013, now Pat. No. 9,399,773, which is a continuation-in-part of application No. 13/964,705, filed on Aug. 12, 2013, now Pat. No. 9,422,559, said application No. 15/167,219 is a continuation of application No. 13/964,705, filed on Aug. 12, 2013, now Pat. No. 9,422,559, which is a continuation-in-part of application No. 13/572,263, filed on Aug. 10, 2012, now abandoned, said application No. 14/502,608 is a division of application No. 13/572,263, filed on Aug. 10, 2012, now abandoned, said application No. 14/527,439 is a division of application No. 13/572,263, filed on Aug. 10, 2012, now abandoned, said application No. 15/167,219 is a continuation of application No. 12/792,413, filed on Jun. 2, 2010, now Pat. No. 9,394,538, said application No. 13/964,705 is a continuation-in-part of application No. 12/792,413, filed on Jun. 2, 2010, now Pat. No. 9,394,538, which is a continuation-in-part of application No. 12/318,806, filed on Jan. 8, 2009, now abandoned, and a continuation-in-part of application No. 12/149,725, filed on May 7, 2008, now Pat. No. 9,567,591.

(60) Provisional application No. 62/262,280, filed on Dec. 2, 2015, provisional application No. 61/761,890, filed on Feb. 7, 2013, provisional application No. 61/746,786, filed on Dec. 28, 2012, provisional application No. 61/522,843, filed on Aug. 12, 2011, provisional application No. 61/323,190, filed on Apr. 12, 2010, provisional application No. 61/272,169, filed on Aug. 26, 2009.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 15/1135* (2013.01); *C12N 2310/14* (2013.01); *C12N 2310/141* (2013.01); *C12N 2310/531* (2013.01); *C12N 2320/30* (2013.01); *C12N 2320/32* (2013.01); *C12N 2330/50* (2013.01); *C12N 2330/51* (2013.01)

(58) Field of Classification Search
None
See application file for complete search history.

(56) References Cited

FOREIGN PATENT DOCUMENTS

WO    WO 2005/056797    *  6/2005

OTHER PUBLICATIONS

Gou, D. et al. ("Gou"; Physiological Genomics 2007, 31(3) 554-562 (Year: 2007).*

* cited by examiner

*Primary Examiner* — James D Schultz
(74) *Attorney, Agent, or Firm* — Knobbe Martens Olson & Bear LLP

(57) ABSTRACT

This invention generally relates to a composition and method of using mam-made small RNAs, such as small interfering RNAs (siRNA), microRNAs (miRNA) and their hairpin-like precursors (pre-miRNA), as tumor suppressing anti-cancer drugs for treating human tumors and cancers, in particular, but not limited, for treating skin (melanoma), blood (leukemia), prostate, breast, liver and lung cancers as well as various neoplastic tumors, such as brain tumors and teratocarcinomas that contain a variety of tumorous and cancerous cells derived from all three germ layers of tissues, including ectoderm, mesoderm and endoderm. More specifically, the present invention relates to the use of miR-302-like siRNA (siR-302) and/or miR-302 precursors (pre-miR-302) for developing novel medicines and therapies against a variety of human cancers, in particular lung cancers.

20 Claims, 28 Drawing Sheets

Specification includes a Sequence Listing.

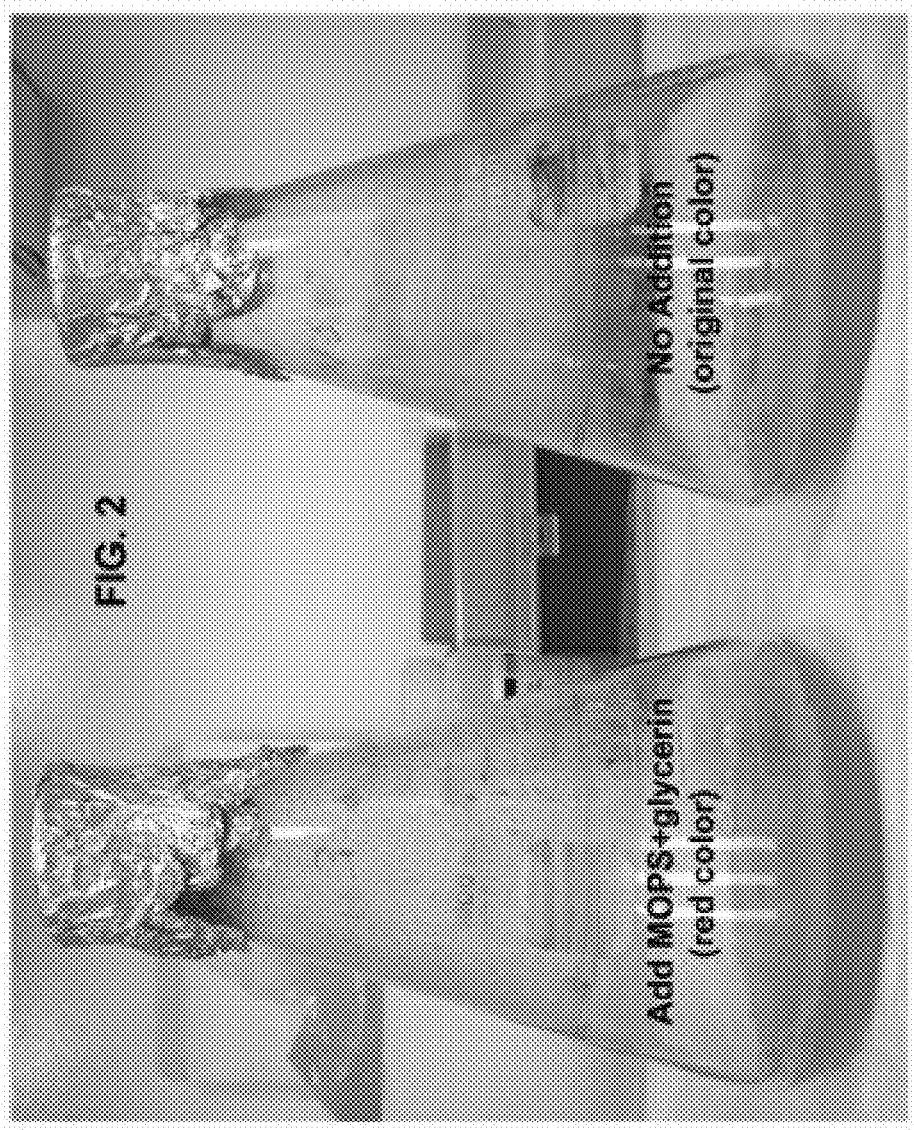

small RNAs extracted from blank *E. coli* competent cells (control)

| Rpter Index | Reporter Name | p-value | Group 1 #1 Mean | Group 2 #2 Mean | Log2 (G2/G1) |
|---|---|---|---|---|---|
| 445 | hsa-miR-302c-5p | 1.28E-03 | 0 | 52,804 | 22.65 |
| 443 | hsa-miR-302a-5p | 1.39E-03 | 0 | 26,579 | 21.85 |
| 441 | hsa-miR-302a-3p | 1.52E-03 | 0 | 66,718 | 22.92 |
| 444 | hsa-miR-302c-3p | 3.51E-03 | 0 | 15,973 | 20.71 |
| 447 | hsa-miR-302d-5p | 2.23E-03 | 3 | 22,124 | 12.87 |
| 313 | hsa-miR-302b-5p | 3.08E-03 | 1 | 940 | 3.75 |
| 442 | hsa-miR-302d-3p | 4.08E-03 | 0 | 9,579 | 18.53 |
| 591 | hsa-miR-320b-3p | 4.08E-03 | 6 | 1,963 | 2.23 |
| 131 | hsa-miR-1275 | 8.78E-02 | 749 | 364 | -1.22 |

Following transcripts are not statistically significant due to low signals (signal < 500)

| 554 | hsa-miR-3177-3p | 2.08E-03 | 402 | 76 | -2.40 |
| 986 | hsa-miR-4459 | 3.59E-03 | 66 | 135 | 1.04 |
| 967 | hsa-miR-4442 | 4.32E-03 | 32 | 65 | 1.02 |
| 1298 | hsa-miR-4758-5p | 4.08E-03 | 7 | 74 | 3.45 |
| 993 | hsa-miR-4466 | 5.70E-02 | 58 | 137 | 1.23 |
| 1120 | hsa-miR-4649-5p | 5.76E-02 | 187 | 385 | 1.04 |
| 1500 | hsa-miR-5195-3p | 5.81E-02 | 49 | 316 | 2.68 |
| 851 | hsa-miR-4253 | 5.86E-02 | 296 | 136 | -1.12 |
| 299 | hsa-miR-146a-5p | 5.93E-02 | 7 | 62 | 3.21 |
| 1156 | hsa-miR-4668-5p | 7.08E-02 | 315 | 70 | -2.17 |
| 974 | hsa-miR-4447 | 7.41E-02 | 13 | 89 | 2.76 |
| 1251 | hsa-miR-4728-3p | 7.96E-02 | 42 | 16 | -1.42 |
| 750 | hsa-miR-146a-3p | 8.97E-02 | 23 | 88 | 1.92 |
| 870 | hsa-miR-4270 | 9.39E-02 | 29 | 113 | 1.95 |
| 1123 | hsa-miR-4651 | 9.46E-02 | 25 | 116 | 2.19 |

FIG. 13A

Sequence of the miR-302 Family

```
  1 AATTTTTTC TTCTAAAGTT ATGCCATTT GTTTCTTTC TCCTCAGCTC TAAATACTCT
 61 GAAGTCCAAA GAAGTGTAT GTTGGGTGG CTCCCTTCAA CTTAACATG GAAGTGCTTT     302B
121 CTGTGACTTT AAAGTAAGT GCTTCCATGT TTAGTAGGA GTGAATCCAA TTTACTTCTC
181 CAAAATAGAA CACGCTAACC TCATTTGAAG GGATCCCTT TGTTTAACA TGGGGTAACC    302C
241 TGCTGTGTGA AACAAAGTA AGTGCTTCCA TGTTTCAGTG GAGTGTCTC CAAGCCAGCA
301 CACCTTTTGT TACAAAATTT TTTGTTATT GTGTTTAAG GTTACTAAGC TTGTTACAGG
361 TTAAAGGATT CTAACTTTTT CCAAGACTGG GCTCCCCAC ACTTAAAGTG GATGTACTT     302A
421 GCTTTGAAAC TAAAGAAGTA AGTGCTTCCA TGTTTTGGTG ATGGTAAGTC TTCTTTTTAC
481 ATTTTATTA TTTTTTAGA AATAACTTT ATTGTATTGA CCGCAGCTCA TATATTTAAG
541 CTTTATTTTG TATTTTTACA TCTGTGTTAAGG GGCCCCCTCT ACTTAACATG GAAGCACTT  302D
601 GCTGTGACAT GACAAAATA AGTGCTTCCA TGTTTGAGTG TGGTTGTTCC TACCTAATCA
661 GCAATTGAGT TAACGCCCAC ACTGTGTGCA GTTCTTGGCT ACAGGCCATT ACTGTTGCTA
```

FIG. 13B
pro-miR302a
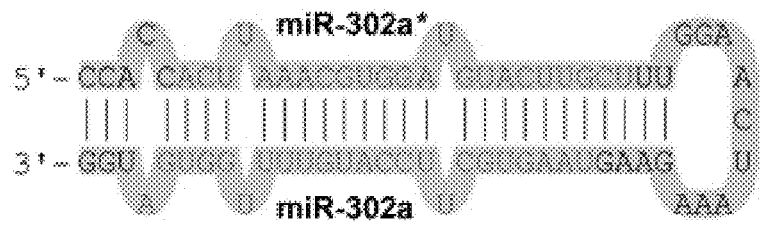
pro-miR-302b
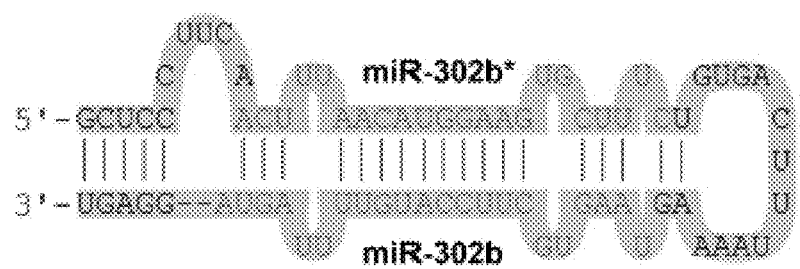
pro-miR-302c
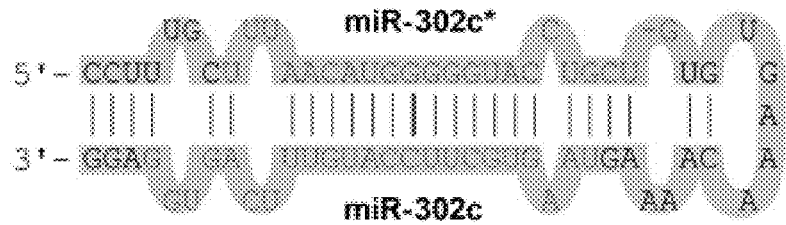
pro-miR-302d
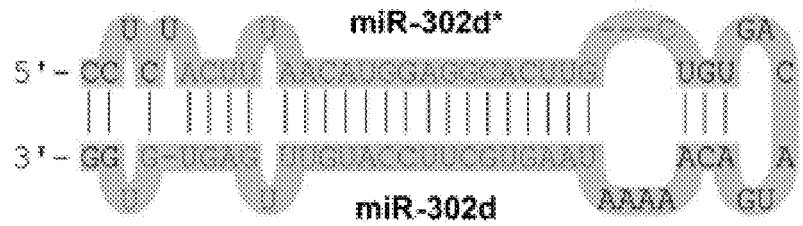

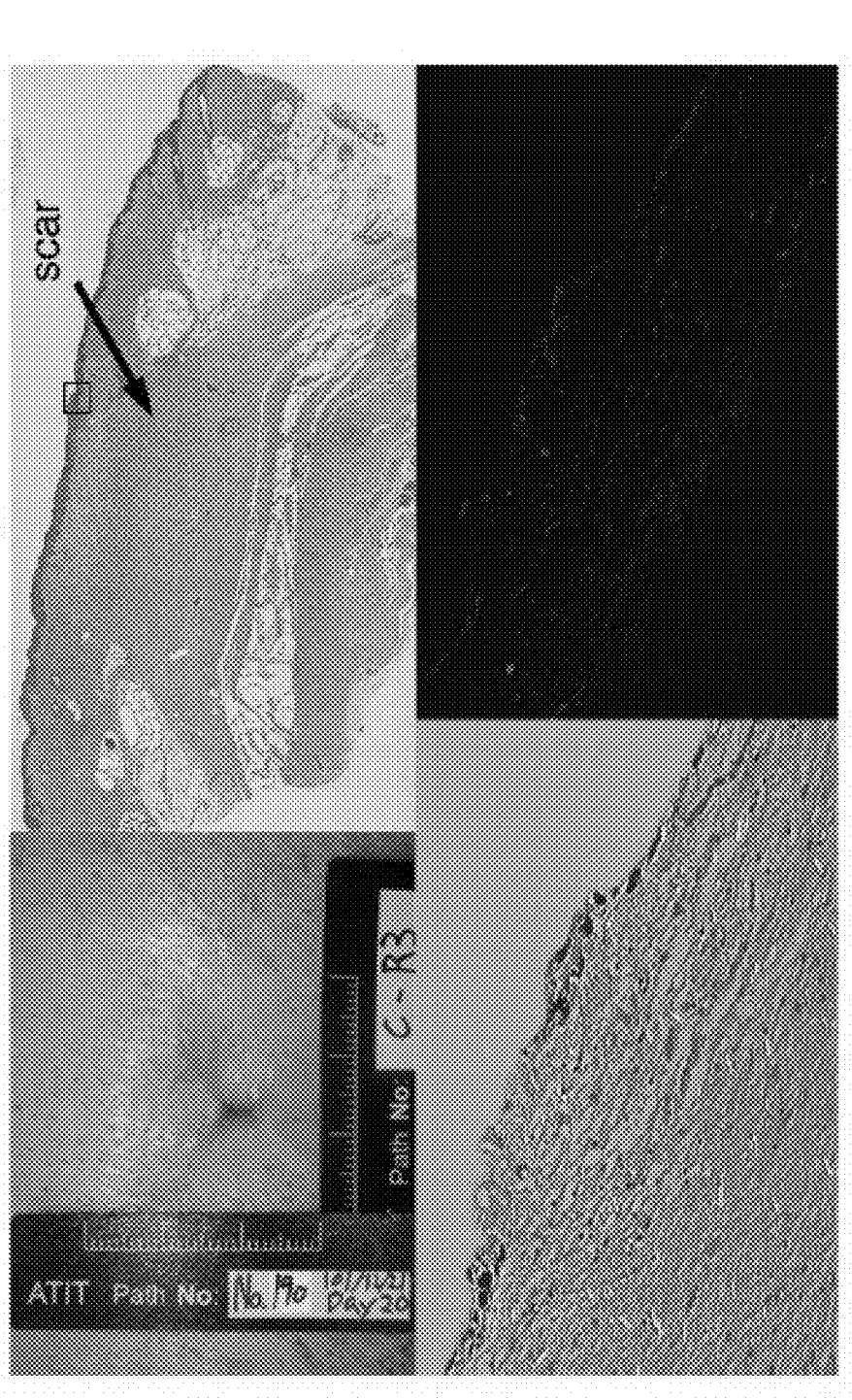
FIG. 17A Example of control section shows large area of scar tissue underneath (190-CR3)

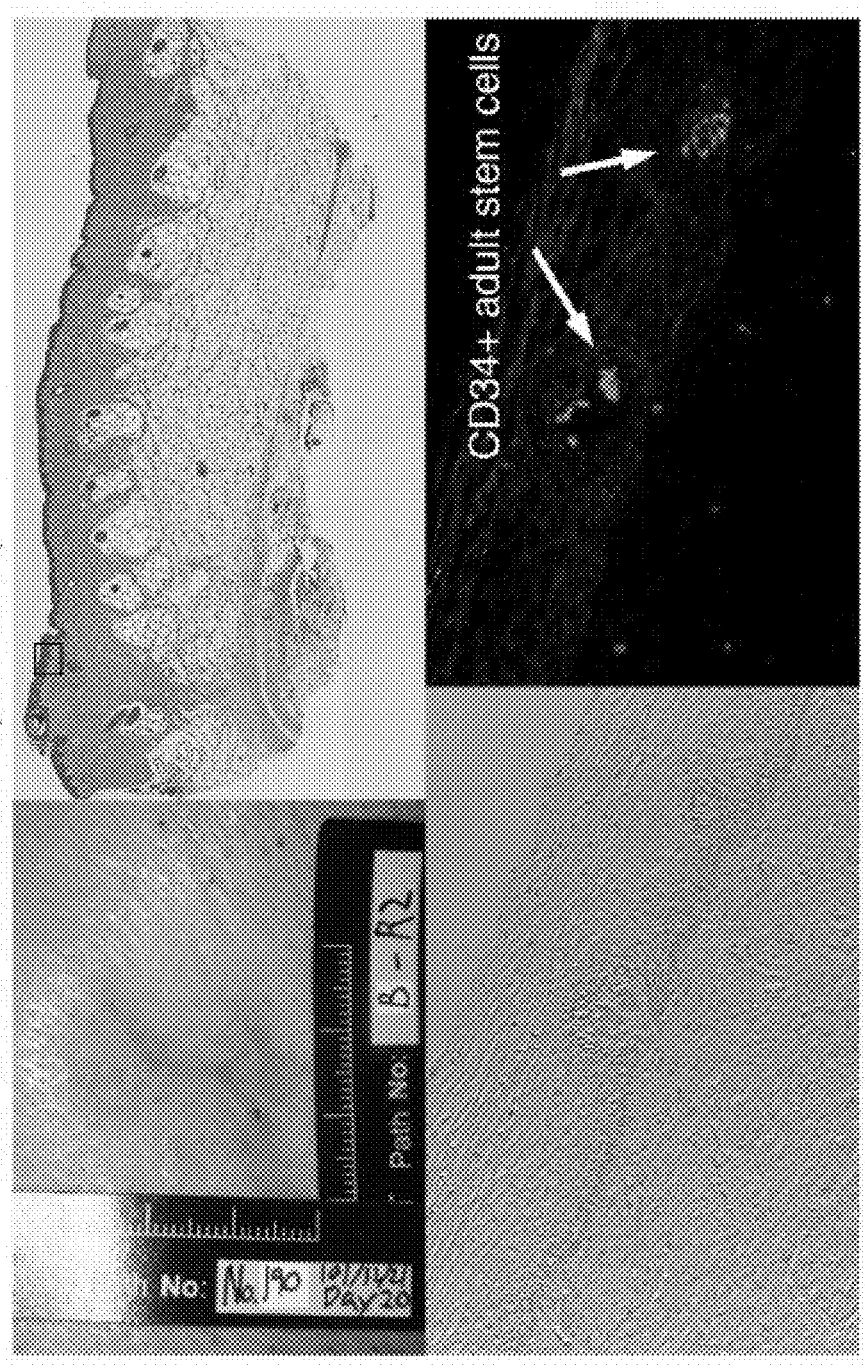

FIG. 20

| | EGFR | p53 | K-ras | Colony formation ability | Effects on growth | Effects on colony formation |
|---|---|---|---|---|---|---|
| PC9/IR | del19 | R248Q | WT | | N.D. | sensitive |
| H1650 | del19 | WT | A183T | | N.D. | sensitive |
| CL1-0 | WT | R248W | N.A. | | sensitive | partial sensitive |
| A549 | WT | WT | G12S | | partial sensitive | partial sensitive |

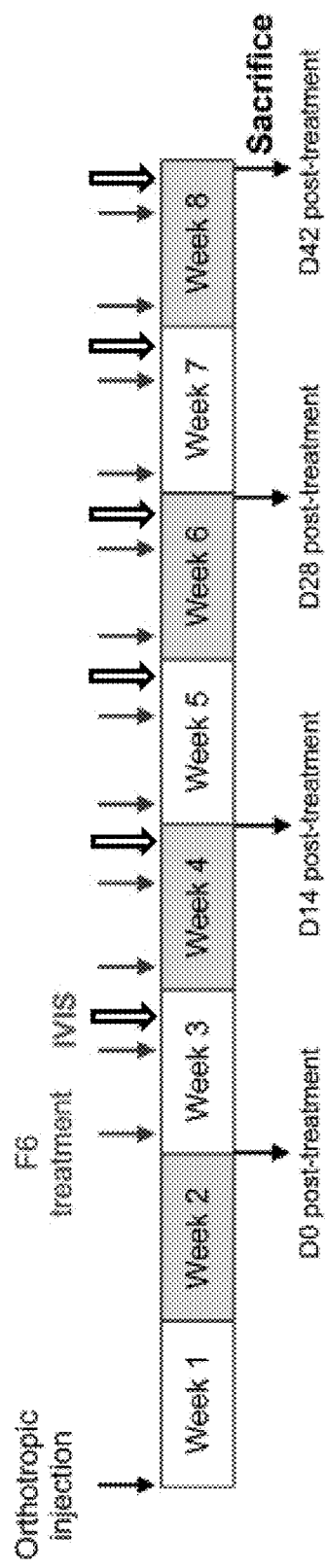
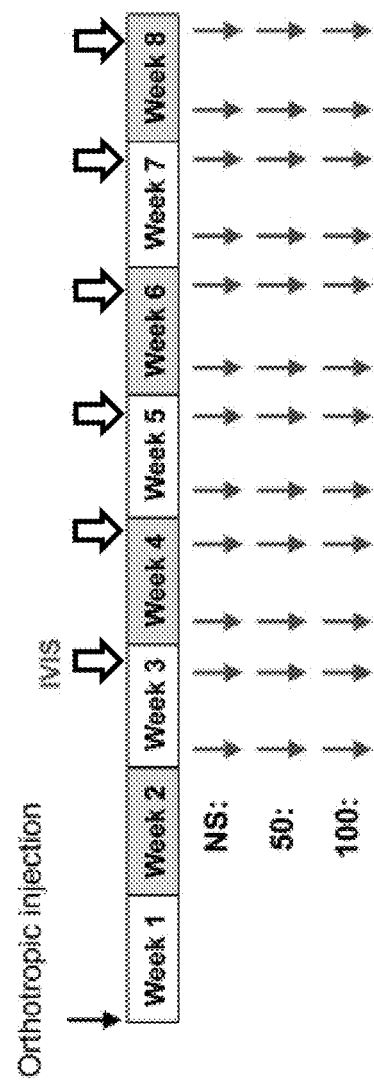
FIG. 21A
FIG. 21B

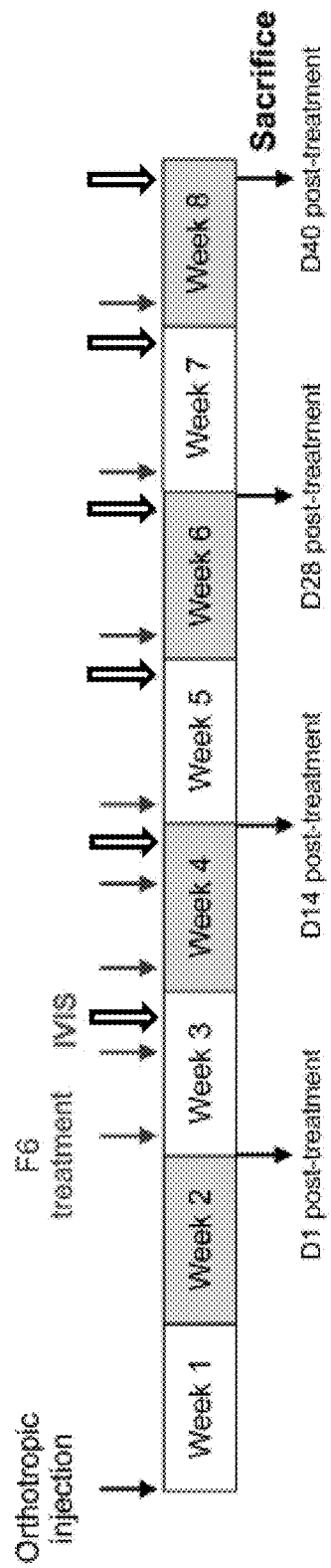
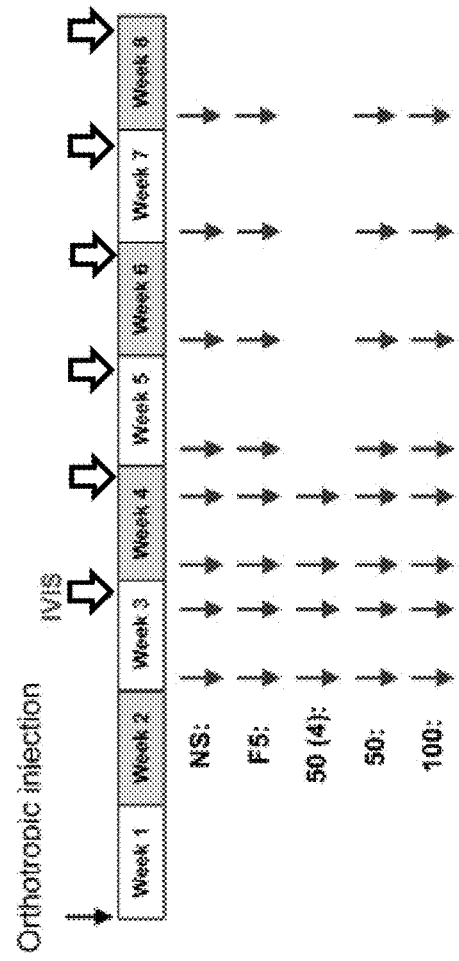
FIG. 23A
FIG. 23B

SEQUENCE LISTING

```
<160> NUMBER OF SEQ ID NOS: 12

<210> SEQ ID NO 1
<211> LENGTH: 23
<212> TYPE: RNA
<213> ORGANISM: human

<400> SEQUENCE: 1
ucaccaaaac auggaagcac uua                                              23

<210> SEQ ID NO 2
<211> LENGTH: 23
<212> TYPE: RNA
<213> ORGANISM: human

<400> SEQUENCE: 2
acuuaaacgu ggauguacuu gcu                                              23
```

```
<210> SEQ ID NO 3
<211> LENGTH: 17
<212> TYPE: RNA
<213> ORGANISM: human

<400> SEQUENCE: 3
uaagugcuuc cauguuu                                                        17

<210> SEQ ID NO 4
<211> LENGTH: 69
<212> TYPE: RNA
<213> ORGANISM: human

<400> SEQUENCE: 4
ccaccacuua aacguggaug uacuugcuuu gaaacuaaag aaguaagugc uuccauguuu          60
uggugaugg                                                                 69

<210> SEQ ID NO 5
<211> LENGTH: 720
<212> TYPE: RNA
<213> ORGANISM: human

<400> SEQUENCE: 5
aauuuuuuuc uucuaaaguu augccauuuu guuuucuuuc uccucagcuc uaaauacucu          60
gaaguccaaa gaaguuguau guugggugggg cucccuucaa cuuuaacaug gaagugcuuu       120
cugugacuuu aaaaguaagu gcuuccaugu uuuaguagga gugaauccaa uuuacuucuc        180
caaaauagaa cacgcuaacc ucauuugaag ggauccccuu ugcuuaaaca uggggguacc        240
ugcugugugu aacaaaagua agugcuucca uguucagug gaggugucuc caagccagca        300
caccuuuugu uacaaaauuu uuuuguuauu uguuuuaag guuacuaagc uuguuacagg         360
uuaaaggauu cuaacuuuuu ccaagacugg gcuccccacc acuuaaacgu ggauguacuu        420
gcuuugaaac uaagaaguaa agugcuucca uguuuuggug augguaaguc uucuuuuuac       480
auuuuuauua uuuuuuuaga aaauaacuuu auuguauuga ccgcagcuca uauauuuaag       540
cuuuauuuug uauuuuuaca ucuguuaagg ggccccccucu acuuuaacau ggaggcacuu      600
gcugugacau gacaaaaaua agugcuucca uguuugagug uggugguucc uaccuaauca       660
gcaauugagu uaacgcccac acugugugca guucuuggcu acaggccauu acuguugcua       720

<210> SEQ ID NO 6
<211> LENGTH: 69
<212> TYPE: RNA
<213> ORGANISM: human

<400> SEQUENCE: 6
ccaccacuua aacguggaug uacuugcuuu gaaacuaaag aaguaagugc uuccauguuu          60
uggugaugg                                                                 69

<210> SEQ ID NO 7
<211> LENGTH: 73
<212> TYPE: RNA
<213> ORGANISM: human

<400> SEQUENCE: 7
gcucccuuca acuuuaacau ggaagugcuu ucgugacuu uaaaaguaag ugcuuccaug           60
uuuuaguagg agu                                                            73
```

```
<210> SEQ ID NO 8
<211> LENGTH: 68
<212> TYPE: RNA
<213> ORGANISM: human

<400> SEQUENCE: 8
ccuuugcuuu aacauggggg uaccugcugu gugaaacaaa aguaagugcu uccauguuuc      60
aguggagg                                                              68

<210> SEQ ID NO 9
<211> LENGTH: 68
<212> TYPE: RNA
<213> ORGANISM: human

<400> SEQUENCE: 9
ccucuacuuu aacauggagg cacuugcugu gacaugacaa aaauaagugc uuccauguuu      60
gagugugg                                                              68

<210> SEQ ID NO 10
<211> LENGTH: 23
<212> TYPE: DNA
<213> ORGANISM: human

<400> SEQUENCE: 10
tcactgaaac atggaagcac tta                                             23

<210> SEQ ID NO 11
<211> LENGTH: 27
<212> TYPE: DNA
<213> ORGANISM: human

<400> SEQUENCE: 11
gaggctggag cagaaggatt gctttgg                                         27

<210> SEQ ID NO 12
<211> LENGTH: 27
<212> TYPE: DNA
<213> ORGANISM: human

<400> SEQUENCE: 12
ccctcctgac ccatcacctc caccacc                                         27
```

COMPOSITION AND METHOD OF USING MIR-302 PRECURSORS AS ANTI-CANCER DRUGS FOR TREATING HUMAN LUNG CANCER

INCORPORATION BY REFERENCE TO ANY PRIORITY APPLICATIONS

Any and all applications for which a foreign or domestic priority claim is identified in the Application Data Sheet as filed with the present application are hereby incorporated by reference.

The present application claims priority to the U.S. patent application Ser. No. 13/572,263 filed on Aug. 10, 2012, Ser. No. 14/502,608 filed on Sep. 30, 2014, and Ser. No. 14/527,439 filed on Oct. 29, 2014, all of which are entitled "An Inducible Gene Expression Composition for Using Eukaryotic Pol-2 Promoter-Driven Transcription in Prokaryotes and The Applications Thereof". The present application also claims priority to the U.S. patent application Ser. No. 15/167,219 filed on May 27, 2016, which is entitled "Production and Utilization of A Novel Anti-Cancer Drug in Therapy". The present application further claims priority to the U.S. patent application Ser. No. 15/167,226 filed on May 27, 2016, which is entitled "Use of MicroRNA Precursors as Drugs for Inducing CD34-positive Adult Stem Cell Expansion". The present application is a continuation-in-part application of the U.S. patent application Ser. No. 13/572,263 filed on Aug. 10, 2012, Ser. No. 14/502,608 filed on Sep. 30, 2014, and Ser. No. 14/527,439 filed on Oct. 29, 2014, all of which are entitled "An Inducible Gene Expression Composition for Using Eukaryotic Pol-2 Promoter-Driven Transcription in Prokaryotes and The Applications Thereof". The present application is also a continuation-in-part application of the U.S. patent application Ser. No. 15/167,219 filed on May 27, 2016, which is entitled "Production and Utilization of A Novel Anti-Cancer Drug in Therapy". The present application is further a continuation-in-part application of the U.S. patent application Ser. No. 15/167,226 filed on May 27, 2016, which is entitled "Use of MicroRNA Precursors as Drugs for Inducing CD34-positive Adult Stem Cell Expansion", which are hereby incorporated by reference as if fully set forth herein.

REFERENCE TO SEQUENCE LISTING

A Sequence Listing submitted as in ASCII text file via EFS-Web is hereby incorporated by reference in accordance with 35 U.S.C. § 1.52(e). The name of the ASCII text file for the Sequence Listing is MELLO_004P1_ST25.TXT, the date of creation of the ASCII text file is Feb. 24, 2017, and the size of the ASCII text file is 3.37 KB.

BACKGROUND

Field

This invention generally relates to a composition and method of using recombinant small RNAs, such as small interfering RNAs (siRNA), microRNAs (miRNA) and their hairpin-like precursors (pre-miRNA), as tumor suppressing anti-cancer drugs for treating human tumors and cancers, in particular, but not limited, for treating skin (melanoma), blood (leukemia), prostate, breast, liver and lung cancers as well as various neoplastic tumors, such as brain tumors and teratocarcinomas that contain a variety of tumorous and cancerous cells derived from all three germ layers of tissues, including ectoderm, mesoderm and endoderm. More specifically, the present invention relates to the use of man-made miR-302-like siRNA (siR-302) and/or miRNA precursors (pre-miR-302) for developing novel medicines for a variety of anti-cancer therapies, in particular for human lung cancer treatments. These siRNA/pre-miR-302 drugs can be produced in prokaryotes as expression-competent DNA vectors and/or the resulting hairpin-like RNA products. As prokaryotic cells do not naturally transcribe or process hairpin-like RNAs, of which the structure resembles a transcriptional termination code in the gene expression systems of prokaryotes, and further in view of the lack of several essential enzymes such as type-II RNA polymerases (Pol-2) and RNaseIII Dicers in prokaryotes, the present invention further teaches a novel gene expression method for expressing pre-miRNAs in prokaryotes, or called prokaryote-produced miRNA precursors (pro-miRNA), using a newly found hairpin-like RNA transcription mechanism in prokaryotes (which is first disclosed in our priority of U.S. patent application Ser. No. 13/572,263). In addition, since miR-302 is a tumor-suppressor miRNA in human embryonic stem cells (hESCs), our findings presented in this invention can be further used to design and develop new medicines, vaccines and/or therapies useful for treating other tumor- and cancer-associated diseases.

Description of the Related Art

Stem cells are a resourceful treasure box containing numerous effective ingredients useful for stimulating new cell growth and tissue regeneration, repairing or rejuvenating damaged/aged tissues, treating aging-related diseases, and preventing tumor formation and cancer progression. Hence, it is conceivable that we can use these stem cells as a tool for screening, identifying and producing these stem cell-specific ingredients for developing novel medicines and therapies directed against a variety of human diseases. As a result, the medicines and therapies so obtained can be used in many pharmaceutical and therapeutic applications, such as a biomedical kit, device and apparatus for research, diagnosis, and/or treatment, or a combination thereof.

MicroRNA (miRNA) is one of the main effective ingredients in human embryonic stem cells (hESCs). Major hESC-specific miRNA species include, but not limited, members of the miR-302 family, miR-371~373 family, and miR-520 family. Among them, the miR-302 family has been found to play a functional role in tumor suppression (Lin et al., 2008 and 2010; U.S. Pat. Nos. 9,394,538, 9,399,773, and 9,422,559 to Lin et al.). MiR-302 contains eight (8) familial members (miR-302s), including four (4) sense miR-302 (a, b, c, and d) and four (4) antisense miR-302* (a*, b*, c*, and d*). These sense and antisense miRNA members are partially matched and can form double-stranded duplexes to each other. Precursors of miR-302 are formed by miR-302a and a* (pre-miR-302a), miR-302b and b* (pre-miR-302b), miR-302c and c* (pre-miR-302c), and miR-302d and d* (pre-miR-302d) with a link sequence in one end (stem loop). In order to activate miR-302 function, miR-302 precursors (pre-miR-302s) are first processed into mature miR-302s by cellular RNaseIII Dicers and further form RNA-induced silencing complexes (RISCs) with certain argonaute (AGO) proteins, subsequently leading to either RNA interference (RNAi)-mediated direct degradation or translational suppression of many targeted gene transcripts (mRNAs), in particular including some major oncogene mRNAs as disclosed in our previous U.S. Pat. Nos. 9,394,538, 9,399,773, and 9,422,559 (Lin et al).

MiR-302 is the most abundant non-coding (ncRNA) species found in hESCs and induced pluripotent stem cells (iPSCs). Our previous studies have shown that ectopic overexpression of miR-302 over the level found in hESC H1 or H9 cells is able to reprogram both human normal and cancerous cells to hESC-like iPSCs with almost no tumorigenecity similar to the pluripotent stem cells of a morula-stage early human zygote (Lin et al., 2008, 2010 and 2011; FP 2198025 to Lin et al.; U.S. patent application Ser. No. 12/149,725 and Ser. No. 12/318,806 to Lin et al.; U.S. Pat. No. 9,394,538 to Lin et at). Relative quiescence is a well defined character of these miR-302-induced iPSCs, whereas late blastocyst-derived hESCs and other previously reported three-/four-factor-induced (either Oct4-Sox2-Klf4-c-Myc or Oct4-Sox2-Nanog-Lin28) iPSCs all present a very fast cell proliferation rate (12-15 hours/cycle) similar to that of a neoplastic tumor/cancer cell (Takahashi et al., 2006; Yu et al., 2007; Wernig et al., 2007; Wang et al., 2008). To disclose this tumor suppression effect of miR-302, we are the first researchers to identify the involvement of two miR-302-targeted G1-checkpoint regulators, including cyclin-dependent kinase 2 (CDK2) (Lin et al., 2010; U.S. Pat. No. 9,394,538 to Lin et al.) and BMI-1 (Lin et al., 2010; U.S. Pat. No. 9,422,559 to Lin et al). Our studies found that miR-302 concurrently silences these two major target genes to inhibit both of the cyclin-E-CDK2 and cyclin-D-CDK4/6 pathways during the G1-S transition of cell cycle, so as to prevent the tumorigenecity of pluripotent stem cells. Furthermore, we also found that the reprogramming function of miR-302 can reprogram high-grade malignant cancers into a low-grade benign or even almost normal state (U.S. Pat. No. 9,399,773 to Lin et al.), via a partial reprogramming mechanism.

However, it is not known whether these previously found tumor suppression functions of miR-302 can be directly used for human lung cancer therapy. Our previous patents and their associated applications can not determine this possibility in view of the varieties of lung cancer types. Unlike other human cancers, the pathological causes of lung cancers are complicated, including air pollution, smoking, asbestosis, virus, long-term inflammation, genetic mutation, and metastasis of other cancers into lung tissues, or even a combination there of. Due to such a great complexity, even an expert can not easily predict the success of a new therapy in other cancers for treating lung cancers. There may require the involvement of more novel therapeutic mechanisms to deal with the complexity of lung cancers.

There is no direct genetic link between miR-302 and lung cancer. The genomic sequence encoding miR-302 is located in the 4q25 locus of human chromosome 4, a conserved region frequently associated with longevity. More precisely, miR-302 is encoded in the intron region of the La ribonucleoprotein domain family member 7 (LARP7) gene and expressed via an intronic miRNA biogenesis pathway that we found (Ying and Lin, 2004; Barroso-delJesus, 2008; FIG. 13; SEQ.ID.NO.5). In our previous studies, we had observed that introduction of miR-302 can stimulate the expression of many other hESC-specific miRNAs, such as miR-92, miR-93, miR-367, miR-371~373, miR-374, and the miR-520 familial members in the transfected cells (Lin et al., 2008, 2010 and 2011; FP 2198025 to Lin et al.; U.S. patent application Ser. No. 12/149,725 and Ser. No. 12/318,806 to Lin et al.). Analyses using the online "TARGETSCAN" and "PICTAR-VERT" programs further revealed that miR-302 shares over 400 target genes with these stimulated miRNAs, suggesting that they may also play a similar functional role as mir-302. These shared target genes include, but not limited, members of RAB/RAS-related oncogenes, EC T-related oncogenes, pleiomorphic adenoma genes, E2F transcription factors, cyclin D binding Myb-like transcription factors, HMG-box transcription factors, Sp3 transcription factors, transcription factor CP2-like proteins, NFkB activating protein genes, cyclin-dependent kinases (CDKs), MAPK/JNK-related kinases, SNF-related kinases, myosin light chain kinases, TNF-alpha-induce protein genes, DAZ-associated protein genes, LIM-associated homeobox genes, DEAD/H box protein genes, forkhead box protein genes, BMP regulators, Rho/Rac guanine nucleotide exchange factors, IGF receptors (IGFR), endothelin receptors, left-right determination factors (Lefty), cyclins, p53 inducible nuclear protein genes, RB-like 1, RB binding protein genes, Max-binding protein genes, c-MIR cellular modulator of immune recognition, Bcl2-like apoptosis facilitator, protocadherins, TGFβ receptors, integrin 134/138, inhibin, ankyrins, SENP1, NUFIP2, FGF9/19, SMAD2, CXCR4, EIF2C, PCAF, MECP2, histone acetyltransferase MYST3, nuclear RNP H3, and many nuclear receptors and factors. The majority of these target genes are involved in embryonic development and tumorigenecity. Hence, it is conceivable that miR-302 can further stimulate its homologous miRNAs, such as miR-92, miR-93, miR-367, miR-371~373, miR-374, and miR-520, to enhance and/or maintain its functionality.

Although miR-302 is useful for designing and developing novel anti-cancer drugs/vaccines, its production is problematic because natural miR-302 can only be found in human pluripotent stem cells such as hESCs, of which the original source is very limited and highly controversial. Alternatively, synthetic small interfering RNAs (siRNA) may be used to mimic pre-miR-302; yet, since the structure of a pre-miR-302 is formed by two mis-matched strands of miR-302 and miR-302*, those perfectly matched siRNA mimics can not replace the function of miR-302*, of which the sequence is totally different from the antisense strand of siRNA. For example, the antisense strand of siRNA-302a mimic is 5'-UCACCAAAAC AUGGAAGCAC UUA-3' (SEQ.ID.NO.1), whereas native miR-302a* is 5'-ACUUAAACGU GGAUGUACUU GCU-3' (SEQ.ID.NO.2). As the full miR-302 function must result from both of its sense miR-302 and antisense miR-302* strands, many previous reports using siRNA mimics have shown different results from native miR-302 functions in nature. On the other hand, our recent discovery of iPSCs may provide an alternative solution for pre-miR-302 production (EP 2198025 to Lin et al.; U.S. patent application Ser. No. 12/149,725 and Ser. No. 12/318,806 to Lin et al.). Nevertheless, the cost and risk of growing these iPSCs is still too high to be used for industrial production now.

Alternatively, the use of prokaryotic competent cells may be a possible approach for producing human miRNAs and their precursors (pre-miRNAs). However, prokaryotic cells lack several essential enzymes required for eukaryotic miRNA expression and processing, such as Drosha and Dicer proteins. Also, prokaryotic RNA polymerases do not efficiently transcribe small RNAs with high secondary structures, such as hairpin-like pre-miRNAs and shRNAs. In fact, there is no true miRNA species encoded in bacterial genomes and bacteria do not naturally express miRNA because hairpin-like RNA structures like pre-miRNAs are similar to the intrinsic transcription termination codes in prokaryotic gene expression systems (McDowell et al., *Science* 1994). As a result, if we can express human miRNAs in prokaryotes, the resulting miRNAs will remain in their precursor forms similar to pri-miRNA (a large primary cluster of multiple pre-miRNAs) or pre-miRNA (one single hairpin RNA). Yet, as aforementioned, the real challenge is how to force the expression of human miRNAs in prokaryotes. To overcome this problem, our priority inventions of U.S. patent application Ser. No. 13/572,263, Ser. No.

14/502,608 and Ser. No. 14/527,439 have established a method for generating prokaryote-produced microRNAs (pro-miRNA). The pro-miRNAs so obtained have been tested to possess the same sequences, structures and functions as their native pre-miRNA counterparts.

As learning from current textbooks, every ordinary skill person in the art knows very well that prokaryotic and eukaryotic transcription machineries are very different and hence not compatible to each other. For example, based on current understandings, eukaryotic RNA polymerases do not bind directly to a promoter sequence and require additional accessory proteins (cofactors) to initiate transcription, whereas prokaryotic RNA polymerases are single holoenzymes that bind directly to a promoter sequence to start transcription. It is also a common knowledge that eukaryotic messenger RNA (mRNA) is synthesized in the nucleus by type-II RNA polymerases (Pol-2) and then processed and exported to the cytoplasm for protein synthesis, while prokaryotic RNA transcription and protein translation take place simultaneously off the same piece of DNA in the same place. This is because prokaryotes such as bacteria and archaea do not have any nucleus-like structure. Accordingly, these natural differences make a prokaryotic cell difficult or even impossible to produce eukaryotic RNAs using eukaryotic promoters.

Prior arts attempt at producing mammalian peptides and/or proteins in bacterial cells, such as U.S. Pat. No. 7,959,926 to Buechler and U.S. Pat. No. 7,968,311 to Mehta, used bacterial or bacteriophage promoters. For initiating expression, a desired gene was cloned into a plasmid vector driven by a bacterial or bacteriophage promoter. The gene must not contain any non-coding intron because bacteria do not have any RNA splicing machinery to process the intron. Then, the vector so obtained was introduced into a competent strain of bacterial cells, such as *Escherichia coli* (*E. coli*), for expressing the transcripts (mRNAs) of the gene and subsequently translating the mRNAs into proteins. Nevertheless, the bacterial and bacteriophage promoters, such as Tac, Lac, Tc, T1, T3, T7, and SP6 RNA promoters, are not Pol-2 promoters and their transcription activities tend to be an error-prone process, which causes mutations and can not express any hairpin-like RNA structure as reported by McDowell et al (*Science* 1994). In addition, Mehta further taught that glycerol/glycerin might be used to increase the efficiency of bacterial transformation; yet, no teaching was related to enhancement of RNA transcription, in particular Pol-2 promoter-driven prokaryotic RNA transcription. Due to lack of compatibility between eukaryotic and prokaryotic transcription systems, these prior arts were still limited by the use of prokaryotic RNA promoters for gene expression in prokaryotes and none of them were useful for expressing hairpin-like RNAs, such as pre-miRNAs and shRNAs.

Due to system incompatibility, there was no means for producing pre-miRNA/shRNA-like drugs in prokaryotes before our invention of pro-miRNAs. Also, a pre-miRNA/shRNA is sized about 70~85-nucleotides in length which is too large and costly to be made by a RNA synthesis machine. To overcome these problems, the present invention adopts pro-miRNAs. By adding some defined chemical inducers mimicking eukaryotic transcriptional cofactors, we can create a novel adaptation environment for prokaryotic cells to use eukaryotic Pol-2 and Pol-2-like viral promoters for transcribing hairpin-like pre-miRNAs and shRNAs. The advantages are: first, cost-effective mass production due to the fast growth of bacteria; second, easy handling because of no need for growing dedicate hESCs or iPSCs; third, high fidelity productivity in terms of Pol-2 promoter-driven RNA transcription; fourth, high purity of resulting pre-miRNAs and siRNAs due to lack of true miRNA in prokaryotes; and last, no endotoxin, which can be further removed by certain chemical treatments. Therefore, a method of producing high quality and high quantity of pro-miRNAs as drugs for treating human lung cancers is highly desirable.

SUMMARY

The present invention is related to the use of hairpin-like RNAs such as pre-miR-302s (SEQ.ID.NO.6~SEQ.ID.NO.9) and its siRNA mimic (siR-302) for treating human lung cancers. The pre-miR-302 and siR-302 are made by a novel pro-miRNA production method using certain chemical inducers to stimulate and enhance eukaryotic promoter-driven hairpin-like RNA transcription in prokaryotic cells. These chemical inducers include 3-morpholinopropane-1-sulfonic acid [or called 3-(N-morpholino) propanesulfonic acid; MOPS], glycerin (or called glycerol) and ethanol, as well as their functional analogs, such as 2-(N-morpholino)ethanesulfonic acid (MES), 4-(2-hydroxyethyl)-1-piperazineethanesulfonic acid (HEPES) and mannitol. Also, it is conceivable that chemicals with a similar structure like these inducers may share the same functionality. Yet, MOPS is often used as a buffering agent in bacterial cell lysis, ethanol is a well-known sanitizer, and glycerin is frequently used as a bacteriostatic agent in bacterial transformation by destabilizing the bacterial cell walls. In view of these known functionalities of MOPS, ethanol and glycerin, no one would anticipate the use of a 0.001% to 4% (volume/volume) concentration of these chemicals for inducing eukaryotic promoter-driven gene expression in prokaryotes.

Based on the above description, the present invention also contains a design and method for utilizing prokaryotic cells to produce human microRNA precursors (pre-miRNAs) and/or shRNAs as therapeutic drugs and/or vaccines for cancer therapy. More specifically, the present invention is a design and method of utilizing prokaryotic cells to produce a special kind of pre-miRNA-like agents, named prokaryote-produced miRNA precursors (pro-miRNA), that are capable of reprogramming high-grade malignant/metastatic human cancer cells into a low-grade benign or even normal-like state. Preferably, these pro-miRNAs are tumor suppressor microRNAs (TS-miRNA) similar to the precursors of miR-302a, b, c, d, e, and/or f (pre-miR-302s) and their natural familial cluster as well as their manually re-designed small hairpin-like RNAs (shRNAs), and/or a combination thereof. The structures of pre-miR-302-like shRNAs include imperfectly and perfectly matched double helix conformations of the pre-miR-302 stem-arm sequences, which may be formed in a single unit or in a multiple unit cluster. Also, the mismatched part of a pre-miR-302-like shRNA can be located in either stem arm or loop region, containing about 30% to 100% homology to the desired pre-miR-302 sequences. These designs may improve the target specificity and/or reduce the copy number of pro-miR-302 required for effective delivery and cancer therapy. The human cells suitable for such a drug treatment include normal, tumor, and cancerous cells in vitro, ex vivo and/or in vivo.

Preferably, the prokaryotic cells used for the present invention are bacterial competent cells in particular, *Escherichia coli* (*E. coli*), and the chemical inducer is MOPS, ethanol, or glycerin, or a mixture thereof. Also preferably, the eukaryotic RNA promoter used is either a eukaryotic Pol-2 promoter (i.e. EF1alpha promoter) or a Pol-2 compatible (Pol-2-like) viral promoter (i.e. cytomegaloviral CMV promoter). The gene mediated by the eukaryotic RNA promoter may code for either a non-coding or protein-coding RNA, or both (such as an intron-containing gene transcript), selected from the group consisting of microRNA (miRNA), small hairpin RNA (shRNA), small interfering RNA (siRNA), messenger RNA (mRNA), their precursors and homologues, and a combination thereof. For inducing gene expression, the prokaryotic cells are transfected with the eukaryotic RNA promoter-mediated gene and then grown in a culture medium similar to the bacterial culturing medium of Luria-Bertani (LB) broth at 37° C. with addition of the chemical inducer(s) for >24 hours.

To demonstrate the inducibility of said chemical inducers for human microRNA production in prokaryotes, we modified a lentiviral vector pSpRNAi-RGFP-miR302 from our priority U.S. patent application Ser. No. 12/149,725 and Ser. No. 12/318,806 to a new plasmid vector pLenti-EF1a-RGFP-miR302, of which the SpRNAi-RGFP gene expression is driven by a eukaryotic Pol-2 or Pol-2-like promoter, such as EF1alpha and/or CMV promoters, or a recombinant combination of both (FIG. 1A). After that, we transformed *E. coli* competent cells with it and then used the expression of red fluorescent protein (RGFP) as a visible marker for measuring the transcription and production rate of pre-miR-302s (pro-miR-302s), as shown in FIG. 1B. Because the miR-302 familial cluster (SEQ.ID.NO.5) was also further modified to be encoded in the 5'-intron region [e.g. 5'-untranslated region (5'-UTR) or the first intron] of the RGFP gene, the transcription of each RGFP mRNA led to the production of one 4-hairpin miR-302 precursor cluster (pri-miR-302) and/or four 1-hairpin miR-302 precursors (pre-miR-302s), as shown in FIGS. 5 and 6. Due to lack of RNase III Dicer in prokaryotes, the pri-miR-302 transcripts would be eventually broke down (by certain single-strand RNases in *E. coli*) into 1-hairpin pre-miR-302s, all of which could be extracted and further used as therapeutic drugs in the present invention. Broadly speaking 5'-UTR and 3'-UTR are considered as a part of intron in the present invention.

All miR-302 members share a totally identical sequence in their first 5'-seventeen (17) nucleotides 5'-UAAGUGC-UUC CAUGUUU-3' (SEQ.ID.NO.3), and contain >82% homology in their full-length 23-nucleotides of a mature microRNA. Based on the results predicted by online computing programs TARGETSCAN and PICTAR-VERT, these miR-302s concurrently target against almost the same genes, including >600 human genes. In addition, miR-302 also shares many overlapping target genes with mir-92, mir-93, mir-200c, mir-367, mir-371, mir-372, mir-373, mir-374, and mir-520 familial members, all of which may possess similar functions. Most of these target genes are developmental signals and transcriptional factors involved in initiating and/or establishing certain lineage-specific cell differentiation during early embryogenesis (Lin et al., 2008). Many of these target genes are also well-known oncogenes; as a result, miR-302s likely functions as a tumor suppressor to prevent the deviation of normal hESC growth into tumor/cancer cells.

In some embodiments, a method of inhibiting a proliferation of a cancer cell is disclosed. The method includes contacting said cancer cell with an amount of a hairpin-like pre-miRNA containing SEQ.ID.NO.3, the amount being sufficient to inhibit the proliferation of the cancer cell. In some embodiments, the amount is insufficient to inhibit the proliferation of a normal cell. In some embodiments, the amount is within the range of 10 to 200 µg/mL. In some embodiments, the amount is 10 µg/mL, 15 µg/mL, 25 µg/mL, 50 µg/mL, 75 µg/mL, 100 µg/mL, 125 µg/mL, 150 µg/mL, 200 µg/mL, or values therebetween. In some embodiments, the pre-miRNA is a glycylglycerin-encapsulated pro-miR-302. In some embodiments, the cancer cell is in an animal and the glycylglycerin-encapsulated pro-miR-302 is injected into the blood stream of the animal to treat the cancer cell. In some embodiments, the glycylglycerin-encapsulated pro-miR-302 is injected into the animal at a concentration of between 10 to 200 microgram per milliliter of blood of the animal. In some embodiments, the glycylglycerin-encapsulated pro-miR-302 is injected into the animal at a concentration of 10 µg/mL, 15 µg/mL, 25 µg/mL, 50 µg/mL, 75 µg/mL, 100 µg/mL, 125 µg/mL, 150 µg/mL, 200 µg/mL, or values therebetween. In some embodiments, the glycylglycerin-encapsulated pro-miR-302 is injected into the animal at a frequency of twice per day, once per day, twice per week, once per week, once every two weeks, once every four weeks, or values therebetween. In some embodiments, the glycylglycerin-encapsulated pro-miR-302 is injected into the animal at a frequency of twice per week. In some embodiments the cancer cell is from a cancer selected from the group consisting of bladder cancer, lung cancer, brain cancer, liver cancer, breast cancer, melanoma, non-Hodgkin lymphoma, cervical cancer, ovarian cancer, and bone cancer. In some embodiments, the cancer cell is a lung cancer cell.

Induction of Eukaryotic Promoter-Driven Gene Expression in Prokaryotes.

*Escherichia coli* (*E. coli*) competent cells were transformed by the pLenti-EF1alpha-RGFP-miR302 plasmid (FIG. 1A) using a z-competent *E. coli* transformation kit (Zymo Research, Irvine, Calif.) and cultivated in Luria-Bertani (LB) broth supplemented with a mixture of 0.1% (v/v) MOPS and 0.05% (v/v) glycerin (inducers) at 37° C. with frequent agitation at 170 rpm. After overnight incubation, the transformed *E. coli* competent cells expressed highly abundant red RGFP proteins that could be clearly seen in the color of the LB broth, whereas the blank control *E. coli* presented no RGFP, as shown in FIG. 2. The presence of functional RGFP indicated that both of its encoded RNA and protein are successfully produced and processed in the competent cells.

To further confirm the specificity of gene expression induced by the chemical inducers, two transformed *E. coli* strains were prepared: one carried a pLVX-Grn-miR302+367 plasmid vector containing a CMV promoter-driven green fluorescent protein (GFP) gene and the other carried the aforementioned pLenti-EF1alpha-RGFP-miR302 vector. After overnight incubation with only 0.1% (v/v) MOPS, the *E. coli* transformed with pLVX-Grn-miR302+367 were changed to green color while the other with pLenti-EF1alpha-RGFP-miR302 still showed red color, as shown in FIG. 3. This result indicates that the chemical inducers like MOPS can stimulate a specific RNA transcription and its related protein production through either a eukaryotic pol-2 or a pol-2-like viral promoter. Particularly it was noted that the RGFP and GFP production is so abundant that even the *E. coli* cells are visually stained by the respective red and green colors.

Among all chemicals tested in the present invention, the top three most potent inducers are MOPS, glycerin and ethanol, as shown in FIG. 4. The quantitative result of the induced RGFP production was further confirmed by Western blot analysis, as shown in FIG. 5 and Example 3. Bacterial RuvB protein was served as a house-keeping standard to normalize RGFP expression. The inducibility of these identified inducers was also found to be dose-dependent in proportional to their concentrations. Without any treatment, negative control *E. coli* cells just showed their original color in absence of any fluorescent stain. Therefore, according to all these results, the present invention clearly provides a novel chemical-inducible composition and its application for modulating eukaryotic pol-2-driven or pol-2-like viral promoter-driven RNA production in prokaryotic cells. In view of the above demonstration, it is very obvious for an ordinary skill in the art to use other genes or the related cDNAs in place of the RGFP gene for producing functional RNAs and the related proteins in prokaryotes.

Induction of Eukaryotic Promoter-Driven Pre-miRNA Expression in Prokaryotes.

Accompanying the experiments of RGFP induction shown above, we further measured the expression of pri-/pre-miR-302s and their mature miR-302s in the pLenti-EF1alpha-RGFP-miR302-transformed cells with or without chemical induction. As shown in FIG. 6 and Example 4, the quantitative results of induced pri-/pre-miR-302 production have been confirmed by Northern blot analysis. Similar to the results of the RGFP induction in FIGS. 4 and 5, the pri-/pre-miR-302 expression was strongly detected in transformed cells treated with MOPS, glycerin or ethanol, but not blank control, indicating that these chemical inducers indeed stimulated the expression of the encoded pri-/pre-miRNAs in prokaryotic cells through a eukaryotic pol-2 promoter (FIG. 6). Due to the structural similarity of pre-miRNAs and shRNAs, it is obvious for an ordinary skill in the art to use the present invention to produce other kinds of pri-/pre-miRNA species, such as but not limited miR-34, miR-125, miR-146, miR-200, miR-371373 and miR-520. For clarification, these man-made prokaryote-produced pri-/pre-miRNAs are called pro-miRNAs.

Since pLenti-EF1alpha-RGFP-miR302 contains a miR-302 familial cluster located in the 5'-UTR of the RGFP gene (FIGS. 1A and 1B), the induced RGFP gene expression will also generate the miR-302 cluster (pri-miR-302) and its derivative pre-miR-302a, b, c and d (pre-miR-302s) as demonstrated in FIG. 1B. Due to lack of RNase III Dicer in prokaryotes, the pri-miR-302 and pre-miR-302s so obtained were found to remain as hairpin-like microRNA precursors, which are useful for developing therapeutic drugs. In human cells, these pre-miR-302s and pri-miR-302 can be processed into mature miR-302 for eliciting its tumor suppression function. Similarly, the present invention can also be used to produce other kinds of TS-miRNA species and their precursors, such as the miR-34a, miR-146a, miR-373 and miR-520 family.

The resulting pro-miRNAs can be easily extracted from competent *E. coli* cells (Examples 5 and 6) and further purified by high-performance liquid chromatography (HPLC) (FIGS. 10A and 10B). Within the purified pro-miR-302s, we have identified all of the miR-302 familial members (miR-302a, a*, b, b*, c, c*, d, and d*) using analyses of microRNA microarrays (FIGS. 11B and 12) and RNA sequencing [FIGS. 13A (pri-miR-302) and 13B (pre-miR-302s)]. Particularly, the sequencing results showed that these pro-miR-302s all share exactly the same sequences as their natural pre-miR-302 counterparts (FIG. 13B). Furthermore, we have formulated these pro-miR-302s into a soluble drug for IV/in-vivo injection in order to test their therapeutic effects on human liver cancers in vivo (Example 11). As shown in FIG. 14, after 3 injection treatments, the pro-miR-302 drug successfully reduced >90% volume of the engrafted human liver cancers in vivo, shirking the average cancer size to <10% compared to the untreated cancers. Moreover, histological examination with hematoxylin & eosin (H&E) staining further demonstrated that this significantly therapeutic effect was resulted from not only the reported tumor suppression function of miR-302 (Lin et al., 2010) but also another novel reprogramming function that has not yet been observed before. For instance, FIG. 15 clearly showed that the pro-miR-302 drug can reprogram the malignant properties of high-grade human liver cancers in vivo to a much more benign stage almost similar to that of normal liver tissues! These treated cancers can even form normal liver-like structures, such as classical liver lobules, central veins (CV) and portal triads (PT). Therefore, these evidences strongly indicated that pro-miR-302 is able to not only inhibit tumor/cancer cell growth but also reset the malignancy of human cancers to a relatively benign or normal state in vivo, leading to a totally novel therapeutic effect for cancer drug design.

In the present invention, both of the plasmid vector and its encoded non-coding RNAs pre-miRNA/shRNA and pri-miRNA) can be simultaneously amplified in the prokaryotic cells, preferably *E. coli* DH5alpha competent cells (Examples 1, 5 and 6). The method for isolating the amplified pLenti-EF1alpha-RGFP-miR302 plasmid DNA and the transcribed pri-/pre-miR-302s is described in Examples 5 and 6. The technology for delivering plasmid vectors (i.e. pLenti-EF1alpha-RGFP-miR302) into prokaryotic cells is called cell transformation, while the method for delivering the amplified ncRNAs (i.e. pro-/pri-/pre-miR-302s) into eukaryotic cells can be selected from the group consisting of cell endocytosis, chemical/glycerol infusion, peptide/liposomal/chemical-mediated transfection, electroporation, gene gun penetration, microinjection, transposon/retrotransposon insertion, and/or adenoviral/retroviral/lentiviral infection.

Pro-miR-302-Induced Pluripotent Stem Cell Derivation.

MiR-302 has been reported to reprogram mammalian somatic cells to human embryonic stem cell (hESC)-like induced pluripotent stem cells (iPSCs) as demonstrated in our priority U.S. patent application Ser. No. 12/149,725 and Ser. No. 12/318,806. Numerous stem cell applications and therapies have been designed and developed using these iPSCs. Nevertheless, since cultivating these iPSCs and hESCs is very costly and laborious, it is difficult and inefficient to collect miR-302 and its precursors from these pluripotent stem cells. On the other hand, making synthetic shRNA mimics is another possible alternative for pre-miR-302 production; yet, the cost is still very expensive. Also, the similarity between synthetic shRNA and natural pre-miR-302 is very questionable. To solve these problems, the present invention provides a simple, cheap and efficient method for mass production of pre-miR-302 in prokaryotes. Moreover, the extraction and purification of these prokaryote-produced pre-miR-302s (pro-miR-302s) is relatively easy and cost-effective, as shown in FIG. 6 and Example 6 of the present invention.

We have used the pLenti-EF1alpha-RGFP-miR302-transformed *E. coli* cells to produce and isolate high quantity and quality of pLenti-EF1alpha-RGFP-miR302 vector and pro-miR-302s, as shown in Examples 5 and 6. Both pLenti-EF1alpha-RGFP-miR302 and pro-miR-302s are useful for generating iPSCs. Following Example 2, when the pro-miR-302s produced by the present invention were transduced into human skin primary keratinocytes, the transfected keratinocytes were reprogrammed to hESC-like iPSCs that expressed strong hESC marker Oct4 (FIG. 7). In FIG. 8 and Example 8, we further performed bisulfite DNA sequencing assays to show that global DNA demethylation did occur in the promoters of both Oct4 and Sox2 genes, two of the key reprogramming factors as well as hESC markers. As global DNA demethylation and Oct4 expression are known to be the first step of somatic cell reprogramming to form hESC-like iPSCs (Simonsson and Gurdon, Nat Cell Biol. 6: 984-990, 2004), the pro-miR-302s isolated from the MOPS-induced E. coli cell extracts is proven to be as effective as natural pre-miR-302s, which are useful for iPSC derivation. Hence, pro-miR-302 and pre-miR-302 possess the same function in stem cell induction.

Pre-miR-302-induced CD34-positive Adult Stem Cell Expansion and/or Regeneration.

MicroRNA miR-302 has been found to reprogram mammalian somatic cells to hESC-like iPSCs (Lin, 2008, 2010, 2011; U.S. patent application Ser. No. 12/149,725 and Ser. No. 12/318,806 to Lin). Using these iPSCs, many stem cell-associated biomedical applications and therapies have been developed for advancing modern regenerative medicine. Yet, miR-302 is only abundantly found in hESCs rather than differentiated tissue cells. Also, isolation of miR-302 from hESCs is highly debatable, costly and tedious. To solve these problems, our priority of U.S. patent application Ser. No. 15/167,226 has provided a simple, cheap, fast and inducible composition and method for mass production of pre-miRNAs (or called pro-miRNAs) and their siRNA mimics in prokaryotes. Using this method, the production and isolation of pre-miR-302 (pro-miR-302s) from prokaryotic cells is relatively easy and cost-effective, as shown in FIG. 6 and Example 6 of the present invention.

One preferred application of the isolated pre-miR-302s is to induce the expansion of CD34-positive adult stem cells in either normal or cancerous tissues. As shown in FIGS. 17A and 17B, our recent studies in wound healing and cancer therapies using a novel glycylglycerin-formulated pre-miR-302-based drug revealed that treatments of relatively low concentrations (50-500 μg/mL) of the formulated pre-miR-302 as candidate drugs not only greatly enhance scar-less wound healing but also induce CD34-positive adult stem cell expansion around the damaged tissue area in both of mouse and pig skins in vivo. Based on the miR-302-treated (pre-miR-302s+antibiotic ointment) result of FIG. 17B in comparison with that of control (only antibiotic ointment) result of FIG. 17A, it clearly showed a ≥40-fold increase of CD34-positive adult stem cell populations (labeled by green fluorescent anti-CD34 antibodies) in vivo after the pre-miR-302 treatments. The currently known CD34-positive stem cell types include, but not limited to, skin, hair, muscle, blood (hematopoietic), mesenchymal, and neural stem cells. In view of this finding, since miR-302 can be used to induce CD34-positive adult stem cell expansion and/or regeneration in vivo, this therapeutic effect may also help to re-grow and/or revive functional adult stem cells for treating degenerative diseases in humans, such as, but not limited, Alzheimer's diseases, Parkinson's diseases, osteoporosis, diabetes, and cancers.

Utilization of Pro-miR-302 for Liver Cancer Therapy In Vivo.

Our previous studies have demonstrated the feasibility of this approach in treating human hepatocellular carcinoma HepG2 cells in vitro (Lin et al., 2010). As shown in FIG. 9, the treated tumor/cancer cells were reprogrammed to iPSCs (labeled as mirPS-HepG2) and formed embryoid body-like cell colonies. Moreover, miR-302 was also found to induce >95% apoptosis in the treated cancer cell population. The top panels of FIG. 9 further showed that flow cytometry analysis of the DNA content in response to cell cycle stages revealed a significant reduction in the mitotic cell populations after miR-302 treatments (form 45.6% to 17.2%). These results indicated that miR-302 can effectively attenuate the fast cell cycle rate of human liver cancer cells and hence causes significant apoptosis in these cancer cells.

The process of cancer progression was thought to be irreversible due to accumulative gene mutations; yet, the present invention discloses a novel pre-miRNA (pro-miR-302) function that can reprogram high-grade malignant cancers back to a low-grade benign or even normal-like stage in vivo, of which the mechanism may be related to a very rare natural healing process called spontaneous cancer regression. Spontaneous cancer regression occurs rarely at a rate of less than 1 in 100,000 cancer patients. We found that pro-mir-302 treatment is able to increase this rare healing rate to >90% in human liver cancers. As shown in FIG. 14, the therapeutic results of using pro-miR-302s as a drug to treat human liver cancer xenografts in SCID-beige nude mice (n=6) demonstrated that this pro-mir-302 drug successfully reduced cancer sizes from 728±328 mm$^3$ (untreated blank control, C) to 75±15 mm$^3$ (pro-mir-302-treated, T), indicating a ~90% reduction rate in the average cancer size, whereas treatments of other synthetic siRNA mimics (siRNA-302) did not provide any similar therapeutic effect.

Further histological examination (the most right panels of FIG. 14) showed that normal liver lobule-like structures (circled and pointed by a black arrow) were observed only in pro-miR-302-treated cancer grafts but not other treatments or controls, suggesting that a reprogramming mechanism has occurred to reset the malignant cancer cell property back to a relatively normal-like state (Cancer Reversion). This novel reprogramming mechanism is likely resulted from the gene silencing effect of miR-302 on human oncogenes in particular, those mutated oncogenes involved in cancer progression. By silencing those mutated oncogenes, pro-miR-302 is able to reset the cancerous gene expression patterns back to a normal-like state, consequently leading to the therapeutic result of cancer reversion. Nevertheless, this in-vivo reprogramming mechanism may be different from the previously reported somatic cell reprogramming in vitro (Lin et al., 2008 and 2011) because Oct4-positive pluripotent stem cell has not yet been identified in vivo after pro-miR-302 treatments.

More detailed histological examination (FIG. 15) further confirmed that the pro-miR-302 drug did reprogram high-grade (Grade IV) human liver cancer grafts to a more benign low-grade (less than Grade II) state. As shown in FIG. 15, the treated cancer grafts formed classical liver lobules containing central vein (CV)-like and portal triad (PT)-like structures (indicated by black arrows), highly similar to normal liver tissue structures (top). Histological comparison among untreated, siRNA-treated, pro-miR-302-treated human liver cancer grafts and normal liver tissues in vivo (FIG. 16) also showed that the engrafted human liver cancers without treatment (top) aggressively invaded into surrounding normal tissues, such as muscles and blood vessels, and formed massive cell-cell and cancer-tissue fusion structures, demonstrating its high malignancy and metastasis. Treatment of siRNA mimics (siRNA-302) did not significantly reduce the malignancy of the engrafted liver cancers (upper middle), probably due to the short half-life of siRNA in vivo. In contrast, treatment of pro-miR-302 not only reprogrammed the engrafted cancer cells to a normal liver cell-like morphology (no fusion) but also successfully inhibited any cancer invasion into the surrounding tissues (lower middle). Compared to normal liver tissues (bottom), pro-miR-302-treated cancers clearly displayed similar lobule structures, normal gland cell-like arrangements, and very clear boundaries between cell-cell and cancer-tissue junctions (black arrows), suggesting that these treated cancers have been greatly downgraded to a very benign state. Further continuous treatments of the pro-miR-302 drug over six to ten times could completely eliminate the cancer xenografts in all six samples (n=6).

Utilization of Pro-miR-302 for Lung Cancer Therapy In Vivo.

In the present invention, we would like to extend the application of miR-302 treatment in lung cancer therapy. To reach this goal, we first tested the dose-dependent tumor suppression effect of glycylglycerin-encapsulated pro-miR-302 (or called formula #6; F6) on the growth of different lung cancer cell types isolated from patients, and found that the use of 25 to 50 µg/mL of the F6 solution presented the best inhibitory results against all of the tested lung cancer cell proliferation but not normal cell growth in vitro (FIG. 18). In order to further measure the F6 drug potency against the growth of malignant lung cancer cell types, a soft agar colony formation assay was performed. As shown in FIGS. 19A and 19B, we found that the colony formation ability of a typical human malignant lung cancer cell line—A549—in this soft agar system was significantly reduced following F6 treatments, especially in the population of large size colonies (diameter ≥200 µm). This result clearly demonstrated the therapeutic effect of formulated pre-miR-302s on the proliferation of malignant/metastatic lung cancer cells. Furthermore, FIG. 20 revealed the mutation status of several driver genes in a variety of different human lung cancer cell types, including the mutant types of EGFR, p53, and K-ras oncogenes. Pictures shown in the middle column of FIG. 20 are the colonies formed by original cancer cells derived from four different human lung cancer cell lines (types) without any treatment, whereas the panels on the right of the middle column of pictures displayed the inhibitory effects of one F6 treatment on the colony formation of these lung cancer types, of which the resulting drug potency was categorized into four groups: sensitive (reduced >50% in the average colony size), partial sensitive (reduced 25~50%), partial resistant (reduced <25%), and resistant groups (no effect 0%). Taken together, these results confirmed that the designed pro-miR-302 treatment can significantly suppress the growth and colony formation ability of many malignant/metastatic lung cancer types. Particularly, the dramatically drug-sensitive responses of PC9/IR cells also implied a possible counteractive relationship between the tyrosine kinase inhibitor (TKI)-mediated drug resistant pathway and the miR-302-mediated tumor suppression pathway, leading to an improved means for overcoming the drug resistance problem of high-grade malignant/metastatic lung cancers.

In further animal trials using in-vivo orthotopic lung cancer assays (FIGS. 22A-22C), we injected lung cancer cells in the left pleural cavity of each tested mouse to observe the lung to lung metastases. As a result, the cancer nodules found in the right lobes should indicate the metastasis of lung cancers from the primary cancer implant side in the left lobe. FIG. 22A demonstrated the numbers of lung cancer nodules in different experimental and control groups, and FIG. 22B showed the representative photo pictures. In FIG. 22A, the black bar illustrated the nodules found in left lobe, and the white bar showed the nodules found in right lobes. As a result shown in FIGS. 22A and 22B, the nodule numbers in both treatment groups (50 and 100 µg/ml) were significantly decreased in both left and right lobes of lung. The nodule numbers of the control group were 8.7±6.0 and 23.8±12.0 in left and right lobes, respectively. After treatments, the formulated pre-miR-302 (F6) drug successfully reduced the nodules numbers to 1.6±1.9 and 8.3±5.3 in the 50 µg/mL group and 22.5±1.4 and 4.75±3.9 in the 100 µg/mL group, respectively. Furthermore, histological examination (FIG. 22C) of the tissue biopsies showed that typical lung adenocarcinoma structures (circled and pointed by a black arrow) were still observed in all three groups but the tumor numbers and sizes were markedly decreased in the lung tissues of both treatment groups. These data confirmed that the therapeutic potency of this formulated pre-miR-302 (F6) drug is very strong for inhibiting the growth and metastasis of non-small-cell lung cancers (NSCLC) in vivo, particularly in the metastatic lung adenocarcinoma regions.

In order to further evaluate the strong therapeutic effects of the F6 drug on metastatic lung adenocarcinoma, we reduced the treatment frequency of F6 solution in the in-vivo orthotopic lung cancer model (n=11 for both treatment groups and n=5 for control group). As shown in FIGS. 23A and 23B, in this repeated animal trial experiments, mice were treated with F6 via tail vein injection twice per week during the week 3 and 4 and then once a week after week 5 until sacrifice. The applied dosage of F6 was calculated based on the ratio of body weight and total blood volume in order to keep the same F6 concentration treated in all tested mice. Luciferase signals were observed and measured once per week to follow the metastatic cancer growth. In the end, mice were sacrificed on day-42 post-treatment. To further assess the acute toxicity effects of the pre-miR-302 drug, the mice of one tested group were treated only four times of F6 during the week 3 and 4, which was then labeled as the 50 (4) group (FIG. 23B). Furthermore, we also tested the toxicity of glycylglycerin only formula in this in-vivo mouse model to rule out any possible toxicity interference of the drug delivery formulation solution.

The therapeutic results of the second animal trials with a reduced treatment frequency (FIGS. 24A-24C) showed highly consistent anti-cancer effects and nodule suppression patterns as observed in the previous in-vivo orthotopic lung cancer experiments (FIGS. 22A-22C). The nodule numbers of the control group (FIG. 24A) were 9.4±2.2 and 34.8±7.7 in left and right lobes, respectively, while F6 (pre-miR-302) treatment successfully reduced the nodule numbers to 6.75±4.6 and 29.3±3.9 in the 50 (4) µg/mL group, 5.9±2.7 and 16.3±4.4 in the 50 µg/mL group, and 4.3±2.9 and 10.5±4.4 in the 100 µg/mL group. FIG. 24B further demonstrated the representative pictures of all control and treated lung cancer tissues in FIG. 24A. Interestingly, the photos of lung tissues isolated from the treatment groups showed not only a marked decrease of nodule numbers in both left and right lobes but also displayed the healed scar tissues under the lung surface, suggesting that an enhanced normal tissue repairing effect was also stimulated by the F6 treatment in the damaged tissue areas of lung cancers (FIG. 24C). Moreover, further histological examination of the biopsy tissues isolated from the F6 treatment groups showed lymphocyte infiltration in tumors (circled and pointed by a black arrow), indicating that a strong immune response was also stimulated by the F6 treatment, particularly in the tissues of the high-dose F6 treatment group (the 100 µg/mL group; the most right column of FIG. 24C).

NOD SCID mice are immunodeficient. The formulated pre-miR-302 drug re-activated the immune system in the NOD SCID mice. Further, the re-activated immune system in the NOD SCID mice was targeting cancer cells. Thus, pre-miR-302 can be used to activate the immune system and further to activate the immune system to target cancer cells. In some embodiments, the present disclosure is related to re-activating the immune response in patients with an immunodeficiency disorder or disease (e.g. HIV/AIDS). In some embodiments, the formulated pre-miR-302 drug can augment cancer immunotherapy. In certain variants, the formulated pre-miR-302 drug can augment cancer immunotherapy by stimulating an immune response to target cancer cells.

In sum, all of these findings clearly conclude the in-vivo therapeutic effects of F6 (the formulated pre-miR-302 drug) on the growth of highly malignant and metastatic lung cancers, such as NSCLC. These observed therapeutic effects of the present invention include, but not limited, inhibition of lung cancer cell growth, suppression of cancer nodule formation, inhibition of cancer metastasis, prevention of drug resistance, increase of immune system responses, and enhancement of normal tissue repairing in the cancer damaged tissue areas. All of these therapeutic effects of the presently invented pre-/pro-miR-302 drugs are very useful for designing and developing novel medicines and therapies used in a variety of pharmaceutical and therapeutic applications.

A. DEFINITIONS

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more monomeric units of DNA and/or RNA, preferably more than three, and usually more than ten. An oligonucleotide longer than 13 nucleotide monomers is also called polynucleotide. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification, which may be selected from the group consisting of mRNA, hnRNA, rRNA, tRNA, snoRNA, snRNA, pre-microRNA, viral RNA and their RNA precursors as well as derivatives.

Precursor messenger RNA (pre-mRNA): primary RNA transcripts of a protein-coding gene, which are produced by eukaryotic type-11 RNA polymerase machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "-" or "*" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3" can form complete base pairing with its antisense sequence "5'-A-C-G-A-T-3". Also, G and U may form non-Watson-and-Crick pairing such as "5'-T-G-C-3" pairing with "5'-G-U-A-3".

5'-end: a terminus lacking a nucleotide at the 5' position of successive nucleotides in which the 5'-hydroxyl group of one nucleotide is joined to the 3'-hydroxyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides. Also, thymine (T) and uracil (U) are homologous to each other.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3" is complementary to the sequence "5'-A-C-T-3'", and also to "5'-A-C-U-3". Also, G and U may be complementary to each other in an RNA duplex or RNA-DNA pairing sequence. For example, the sequence "5'-U-G-C-3" is complementary to the sequence "5'-G-U-A-3", and also to "5'-G-U-G-3" as well as to "5'-G-C-G-3'" and "5'-G-C-A-3'". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration, such as DNA-DNA, DNA-RNA, and RNA-RNA duplexes as well as any duplex formed by pairing between partial DNA and partial RNA hybrid sequences.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

Gene Silencing Effect: a cell response after a gene function is suppressed, consisting but not limited of cell cycle attenuation, G0/G1-checkpoint arrest, tumor suppression, anti-tumorigenecity, cancer cell apoptosis, and a combination thereof.

Non-coding RNA (ncRNA) an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNA capable of binding to targeted gene transcripts (mRNAs) that have partial complementarity to the sequence of microRNA. Mature microRNA is usually sized about 17-27 oligonucleotides in length and is able to either directly degrade its intracellular mRNA target(s) or suppress the protein translation of its targeted mRNA(s), depending on the complementarity between the microRNA and its target mRNA(s). Native microRNAs are found in almost all eukaryotes, functioning as a defense against viral infections and allowing regulation of specific gene expression during development of plants and animals. In principle, one microRNA often targeted multiple target mRNAs to fulfill its full functionality while on the other hand multiple miRNAs may target the same gene transcripts to enhance the effect of gene silencing.

MicroRNA Precursor (pre-miRNA): hairpin-like single-stranded RNA containing stem-arm and stem-loop regions for interacting with intracellular RNase III Dicer endoribonucleases to produce one or multiple mature microRNAs (miRNAs) capable of silencing a targeted gene or a specific group of targeted genes that contain full or partial complementarity to the mature microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation required for being assembled into an RNA-induced silencing complex (RISC) with some argonaute proteins (AGO).

Prokaryote-produced MicroRNA Precursor (pro-miRNA): hairpin-like RNAs similar to natural microRNA precursors (pre-miRNA) but transcribed from an artificially recombinant microRNA-expressing plasmid driven by a eukaryotic promoter in prokaryotic competent cells. For example, pro-miR-302 is structurally as same as that of pre-miR-302 (FIGS. 13A and 13B) but transcribed from either a pLVX-Grn-miR302+367 or pLenti-EF1alpha-RGFP-miR302 vector in E. coli DH5alpha competent cells (Example 1). As prokaryotic cells normally do not express short hairpin-like RNAs such as eukaryotic pre-miRNAs, of which the structures resemble the transcriptional termination codes in prokaryotes, the production of pro-miRNAs in prokaryotes usually requires the addition of some defined chemical inducer(s) in order to stimulate the eukaryotic promoter-driven hairpin-like RNA transcription (FIGS. 2-4).

Small interfering RNA (siRNA): short double-stranded RNA sized about 18-27 perfectly base-paired ribonucleotide duplexes and capable of degrading target gene transcripts with almost perfect complementarity.

Small or short hairpin RNA (shRNA): single-stranded RNA that contains a pair of partially or completely matched stem-arm nucleotide sequences divided by an unmatched loop oligonucleotide to form a hairpin-like structure. Many natural miRNAs are preserved as a form of shRNA in cells, such as precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, or perhaps binds to, and initiates RNA transcription. For the purposes of the instant invention, a promoter can be a known polymerase or its cofactor binding site, an enhancer and the like, any sequence that can initiate synthesis of RNA transcripts by a desired polymerase.

Eukaryotic Promoter: a sequence of nucleic acid motifs which are required for RNA and/or gene transcription and can be recognized by eukaryotic type II RNA polymerases (Pol-2), Pol-2 equivalent, and/or Pol-2 compatible (Pol-2-like) viral polymerases for initiating the RNA/gene transcription.

Type-II RNA Polymerase (Pol-II or Pol-2) Promoter: an RNA promoter that can be recognized by eukaryotic type-II RNA polymerases (Pol-II or Pol-2) and hence is able to initiate the transcription of eukaryotic messenger RNAs (mRNAs) and/or microRNAs (miRNAs). For example, but not limited, a Pol-2 promoter can be either a mammalian RNA promoter like the EF1alpha promoter or a viral/retroviral promoter like the cytomegaloviral (CMV) promoter, or a combination thereof.

Type-II RNA Polymerase (Pol-II or Pol-2) Equivalent: a eukaryotic transcription machinery selected from the group consisting of mammalian type-II RNA polymerases (Pol-II or pol-2) and compatible (Pol-2-like) viral RNA polymerases.

Pol-II Compatible (Pol-2-like) Viral Promoter: a viral RNA promoter capable of using the eukaryotic Pol-2 or Pol-2 equivalent transcription machineries for initiating gene and/or RNA expression. For example, but not limited, a P01-2-like viral promoter can be a cytomegaloviral (CMV) promoter or a retroviral long terminal repeat (LTR) promoter.

Cistron: a sequence of nucleotides in a DNA molecule coding for an amino acid residue sequence and including upstream and downstream DNA expression control elements.

Intron Excision: a cellular mechanism responsible for RNA processing, maturation and degradation, including RNA splicing, exosome digestion, nonsense-mediated decay (NMD) processing, and a combination thereof.

RNA Processing: a cellular mechanism responsible for RNA maturation, modification and degradation, including RNA splicing, intron excision, exosome digestion, nonsense-mediated decay (NMD), RNA editing, RNA processing, and a combination thereof.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Expression-Competent Vector: a linear or circular form of single- or double-stranded DNA selected form the group consisting of plasmid, viral vector, transposon, retrotransposon, DNA transgene, jumping gene, and a combination thereof.

Antibiotic Resistance Gene: a gene capable of degrading antibiotics selected from the group consisted of penicillin G, streptomycin, ampicillin (Amp), neomycin, G418, kanamycin, erythromycin, paromycin, phophomycin, spectromycin, tetracycline (Tet), doxycycline (Dox), rifapicin, amphotericin B, gentamycin, chloramphenicol, cephalothin, tylosin, and a combination thereof.

Restriction/Cloning Site: a DNA motif for restriction enzyme cleavage including but not limited AatII, AccI, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, Ecl136II, EcoRI/RII/47III/RV, EheI, FspI, HaeIII, HhaI, HinPI, HindIII, HinfI, HpaI/II KasI, KpnI, MaeII/III, MfeI, MluI, MscI, MseI, NaeI, NarI, NcoI, NdeI, NgoMI, NotI, NruI, NsiI, PmlI, Ppu10I, PstI, RsaI, SacI/II, SalI, Sau3AI, SmaI, SnaBI, SphI, SspI, StuI, TaiI, TaqI, XbaI, XhoI, XmaI cleavage site.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Cell Cycle Regulator: a cellular gene involved in controlling cell division and proliferation rates, consisting but not limited of CDK2, CDK4, CDK6, cyclins, BMI-1, p14/p19Arf p15Ink4b, p16Ink4a, p18Ink4c, p21Cip1/Waf1, and p27Kip1, and a combination thereof.

Tumor Suppression Effect: a cellular anti-tumor and/or anti-cancer mechanism and response consisting of but not limited, cell cycle attenuation, cell cycle arrest, inhibition of tumor cell growth, inhibition of cell tumorigenecity, inhibition of tumor/cancer cell transformation, induction of tumor/cancer cell apoptosis, induction of normal cell recovery, reprogramming high-grade malignant cancer cells to a more benign low-grade state (tumor regression), and a combination thereof.

Cancer Therapy Effect: a cell response and/or cellular mechanism resulted from a drug treatment, including, but not limited, inhibition of oncogene expression, inhibition of cancer cell proliferation, inhibition of cancer cell invasion and/or migration, inhibition of cancer metastasis, induction of cancer cell death, prevention of tumor/cancer formation, prevention of cancer relapse, suppression of cancer progression, repairing damaged tissue cells, reprogramming high-grade malignant cancers to a more benign low-grade state (cancer regression/remission), and a combination thereof.

Gene Silencing Effect: a cell response after a gene function is suppressed, consisting of, but not limited, inhibition of oncogene expression, inhibition of cell proliferation, cell cycle arrest, tumor suppression, cancer regression, cancer prevention, cell apoptosis, cell repairing and/or rejuvenation, cell reprogramming reprogramming diseased cells to a relatively normal state (spontaneous healing), and a combination thereof.

Cancer Reversion: a reprogramming mechanism that resets the malignant properties of high-grade cancers back to a relatively normal-like low-grade state in vitro, ex vivo or in vivo.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Transcriptional Inducer: a chemical agent that can induce and/or enhance eukaryotic RNA and/or gene transcription from a pol-2 or pol-2-like promoter in prokaryotic cells. For example, a transcription inducer contains, but not limited, a chemical structure similar to MOPS, ethanol, glycerin, as well as their functional analogs such as 2-(N-morpholino) ethanesulfonic acid (WS), 4-(2-hydroxyethyl)-1-piperazineethanesulfonic acid (HEPES) and mannitol, or a mixture thereof.

Antibody: a peptide or protein molecule having a pre-selected conserved domain structure coding for a receptor capable of binding a pre-selected ligand.

Pharmaceutical and/or Therapeutic Application: a biomedical utilization, device and/or apparatus useful for diagnosis, stem cell generation, stem cell research and/or therapy development, tissue/organ repair and/or rejuvenation, wound healing treatment, tumor suppression, cancer therapy and/or prevention, disease treatment, drug production, and a combination thereof.

B. COMPOSITIONS AND APPLICATIONS

A composition and method for treating human lung cancers using hairpin-like RNAs, comprising: (a) providing at least a hairpin-like RNA containing SEQ.ID.NO.3; and (b) contacting the hairpin-like RNA of (a) with a cancer subject containing at least a lung cancer cell, so as to release the tumor suppression function of the hairpin-like RNAs in the lung cancer cells and thus leading to an anti-cancer therapy effect on the cancer(s). The hairpin-like RNA can be structured in a form of pre-miRNA, shRNA, and siRNA, or a combination thereof. Preferably, the hairpin-like RNA containing SEQ.ID.NO.3 is made by a eukaryotic promoter-mediated transcription system in prokaryotes, wherein the activation of this eukaryotic promoter-mediated transcription system is induced in prokaryotic cells by some chemical inducer agent(s) containing a chemical structure similar to 3-morpholinopropane-1-sulfonic acid (MOPS), ethanol, or glycerin, or a mixture thereof. Preferably, the eukaryotic promoter-mediated transcription system is a Pol-2 and/or Pol-2-like promoter-driven gene expression cassette located in a plasmid vector and the prokaryotes are a competent strain of *Escherichia coli* (*E. coli*) cells, which have been transformed by the plasmid vector containing the eukaryotic promoter-mediated transcription system. Preferably, the condition for inducing eukaryotic promoter-mediated transcription of said hairpin-like RNAs is a bacterial culturing condition such as Luria-Bertani (LB) broth at 37° C. with the addition of said chemical inducer(s).

BRIEF DESCRIPTION OF THE DRAWINGS

Referring particularly to the drawings for the purpose of illustration only and not limitation, there is illustrated:

FIG. 2 depicts the results of bacterial culture broths treated with (left) or without (right) the mixture of 0.1% (v/v) MOPS and 0.05% (v/v) glycerin. The *E. coli* competent cells have been transformed by pLenti-EF1alpha-RGFP-miR302 before the treatment of chemical inducers.

The chemical concentration used can be ranged from about 0.001% to 4%, most preferably, from 0.01% to 1%.

Figure 5:
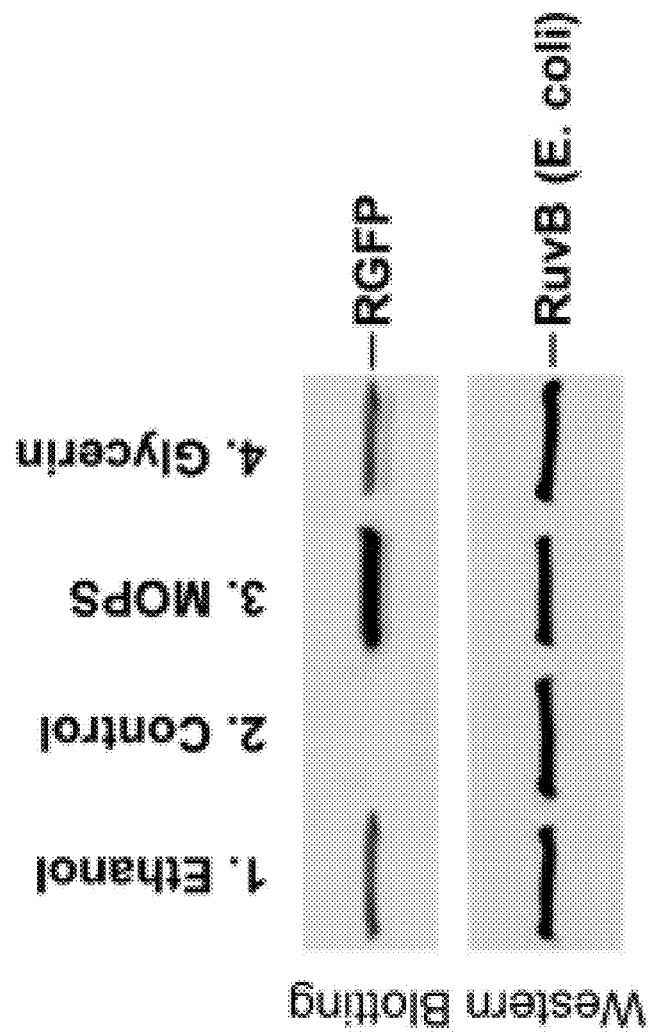

FIG. 5 shows the Western blotting results of red RGFP protein expression induced by MOPS, glycerin and ethanol, respectively. Bacterial RuvB protein was used as a housekeeping standard to normalize the detected RGFP expression. Proteins extracted from blank E. coli cells, i.e. transformed with no vector, were used as a negative control.

Figure 6:
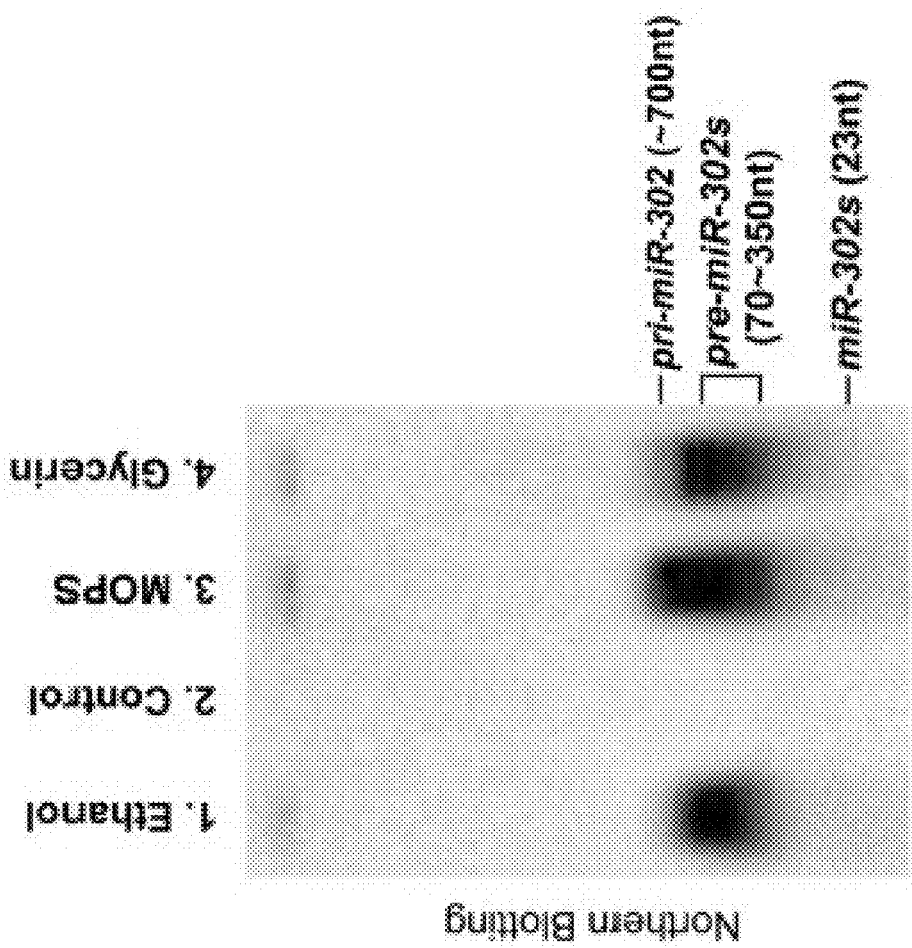

FIG. 6 shows the Northern blotting results of the expression of the miR-302 familial cluster (~700 nt) and its derivative precursors (pre-miR-302s with 1 to 4 hairpins) induced by MOPS, glycerin and ethanol, respectively. RNAs extracted from blank E. coli cells were used as a negative control.

Figure 7:
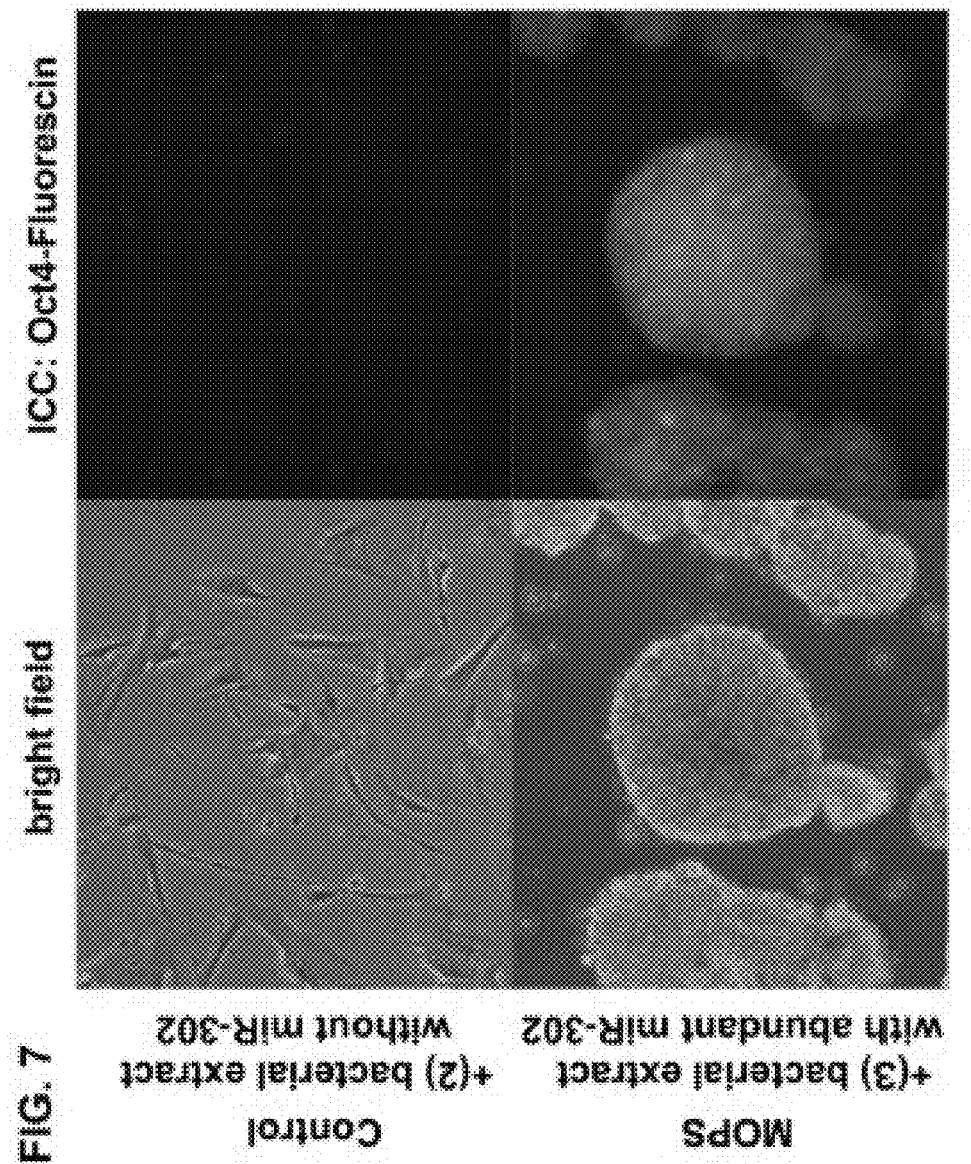

FIG. 7 shows iPSC generation using miR-302 and/or pre-miR-302 isolated from bacterial competent cell extracts (BE), which is confirmed by Northern blot analysis as shown in FIG. 6. As reported, miR-302-reprogrammed iPSCs (or called mirPSCs) form sphere-like cell colonies and express strong Oct4 as a standard hESC marker.

Figure 8:
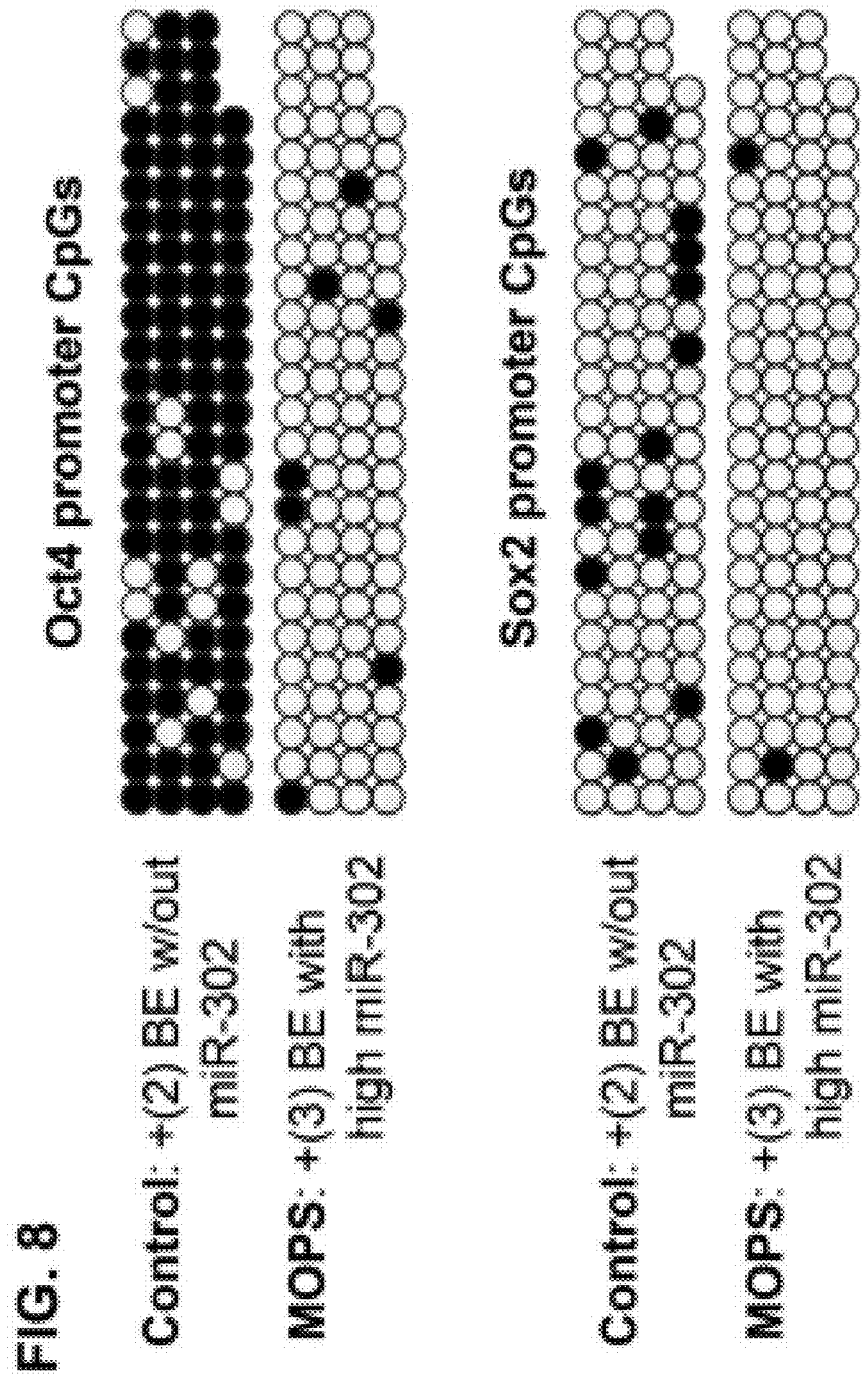

FIG. 8 shows the global DNA demethylation of Oct4 and Sox2 gene promoters induced by the miR-302 and/or pre-miR-302 isolated from bacterial competent cell extracts (BE), which is confirmed by Northern blot analysis as shown in FIG. 6. As demonstrated by Simonsson and Gurdon (Nat Cell Biol. 6, 984-990, 2004), both signs of global DNA demethylation and Oct4 expression are required for somatic cell reprogramming to form iPSCs.

Figure 9:
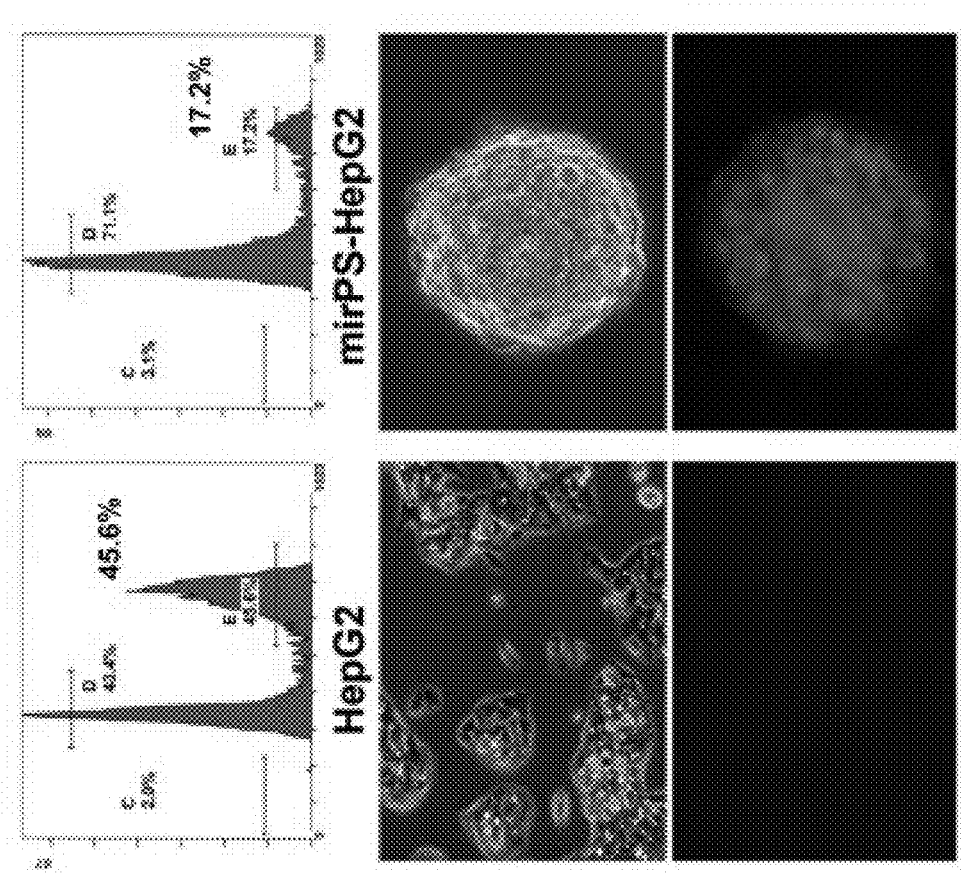

FIG. 9 shows the in vitro tumorigenicity assays of human liver cancer cell line HepG2 in response to miR-302 transfection. The cells obtained after miR-302 transfection are labeled as mirPS-HepG2, indicating the change of their cancer cell properties into an induced pluripotent stem cell (iPSC)-like state. Changes of morphology and cell cycle rate before and after miR-302 transfection were compared. Each cell DNA content respective to cell cycle stages was shown by a peak chart of flow cytometry analysis above the cell morphology (n=3, p<0.01).

Figure 10A:
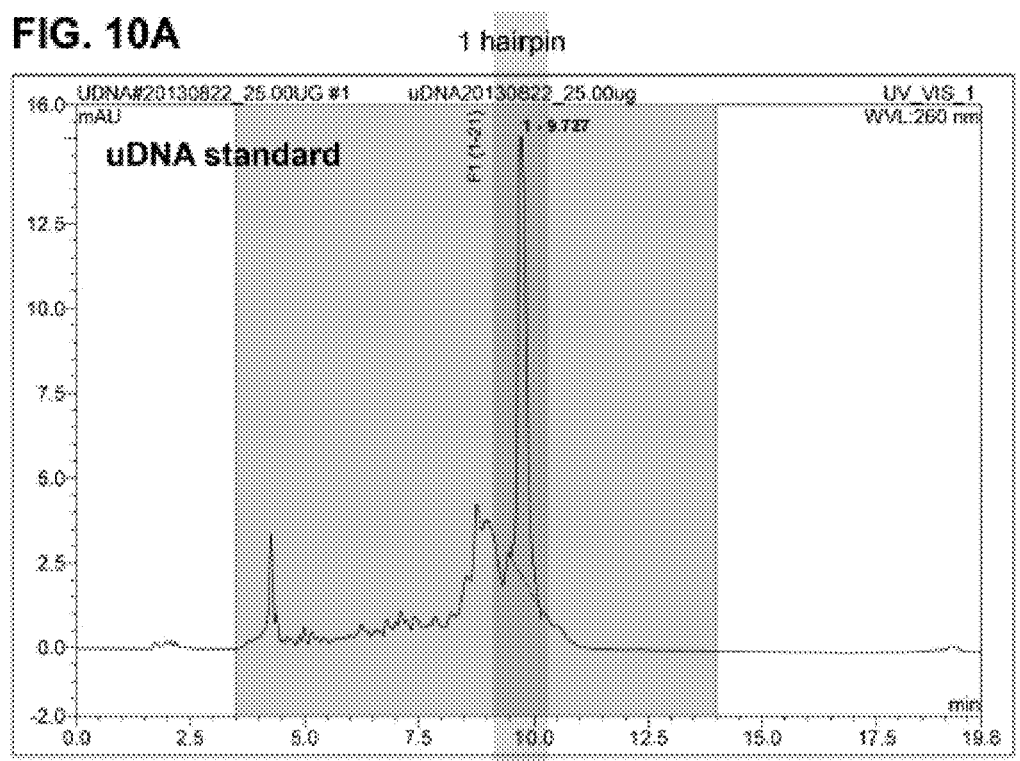
Figure 10B:
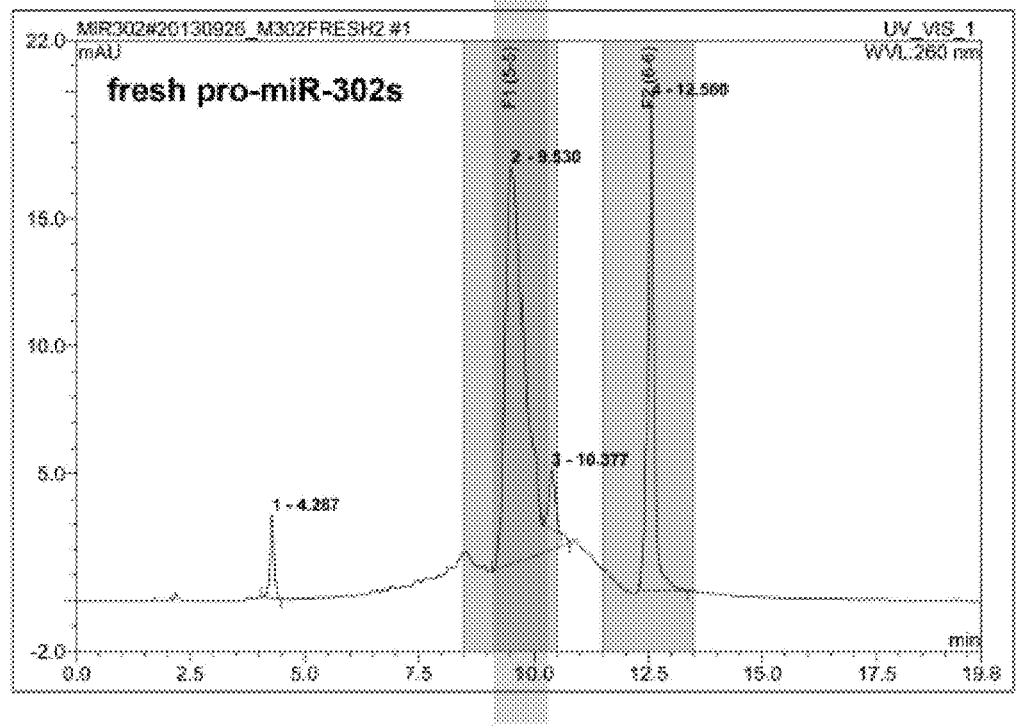

FIGS. 10A and 10B show the results of HPLC purification and analysis using a synthetic standard uDNA (by Sigma-Genosys) and freshly extracted pro-miR-302s isolated from pLenti-EF1alpha-RGFP-miR302-transformed E. coli cells. The standard uDNA was designed to be equal to a natural pre-miR-302a as: 5'-CCACCACUUA AACGUGGAUG UACUUGCUUU GAAACUAAAG AAGUAAGUGC UUCCAUGUUU UGGUGAUGG-3' (SEQ.ID.NO.4).

Figure 11A:
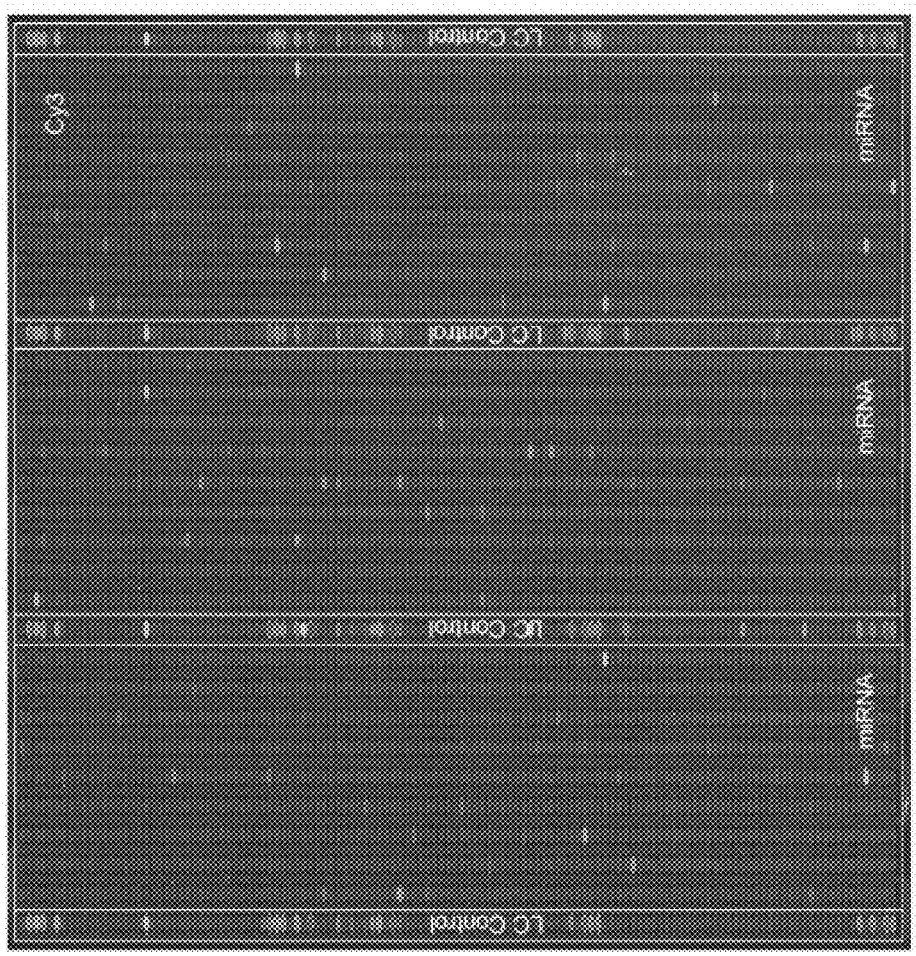
Figure 11B:
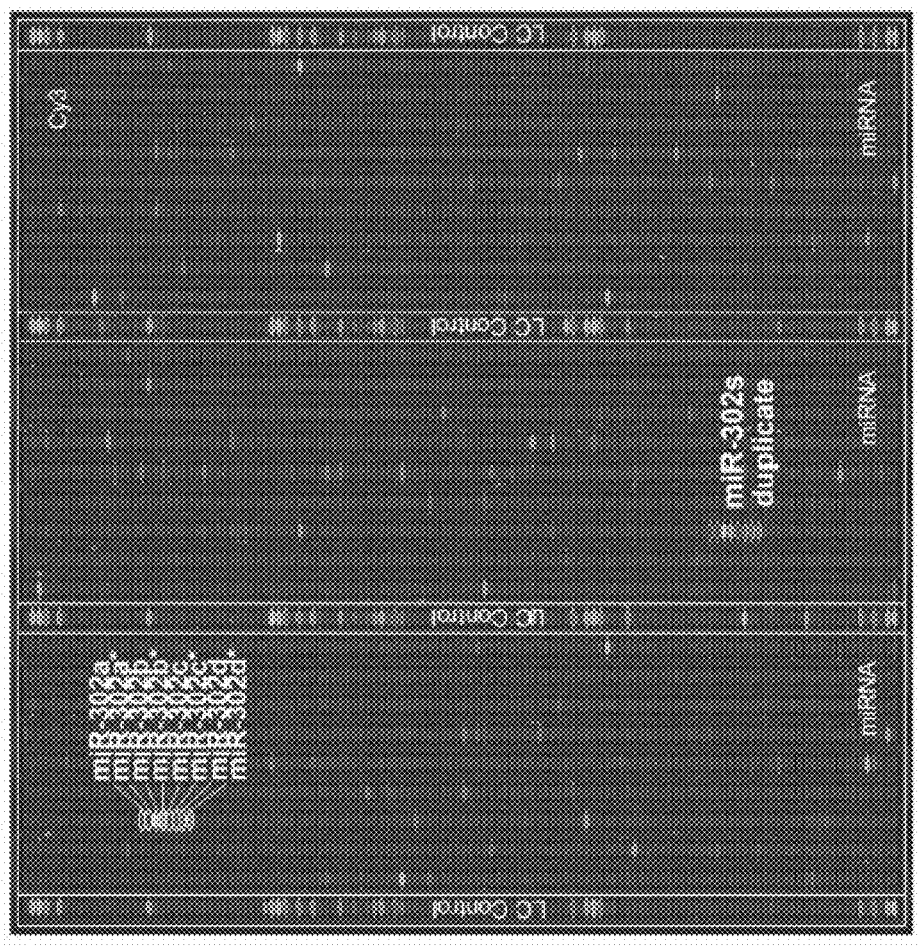

FIGS. 11A and 11B show the results of microRNA (miRNA) microarray analyses using small RNAs extracted from either blank E. coli competent cells or pLenti-EF1alpha-RGFP-miR302 (RGFP-miR302)-transfected cells, i.e. the transformed cells. The extracted small RNAs were further purified by HPLC as shown in the green-labeled area of FIG. 10B. FIG. 11A shows that RNAs from blank E. coli cells present almost no microRNA (green dots mean non-statistically significant whereas red dots indicate positive results). This is because prokaryotes lack several essential enzymes required for microRNA expression and processing, such as Pol-2, Drosha and RNase III Dicer. Also, prokaryotic RNA polymerases do not efficiently transcribe small RNAs with high secondary structures, such as hairpin-like pre-miRNAs and shRNAs. As a result, only using the present invention we can stimulate the expression of specific microRNAs, such as miR-302a, a*, b, b*, c, c*, d and d* as shown in FIG. 11B. In prokaryotic cells. Since prokaryotic cells possess no Dicer, all microRNAs remain in their precursor conformations, such as pri-miRNA (4-hairpin cluster) and/or pre-miRNA (1 hairpin precursor). Taken together, the results of FIGS. 10B and 11B have established two facts as: (1) small RNAs extracted from the RGFP-miR302-transfected cells contain mostly pure miR-302 precursors, and (2) there is almost no other kind of microRNA contamination in the E. coli competent cells.

FIG. 12 shows the lists of expressed microRNAs extracted from either blank E. coli competent cells (Group 1 as shown in FIG. 11A) or pLenti-EF1alpha-RGFP-miR302-transfected cells (Group 2 as shown in FIG. 11B). Signals less than 500 are not statistically significant (as shown in green in FIGS. 11A and 11B), which may be caused by either low copy number expression or high background.

FIGS. 13A and 13B show the sequencing results of the miR-302 familial cluster (family) (13A, SEQ.ID.NO.13, wherein the sequences of pro-miR-302a, pro-miR-302b, pro-miR-302c, and pro-miR-302d are underlined) and the individual pro-miR-302a (SEQ.ID.NO.6), pro-miR-302b (SEQ.ID.NO.7), pro-miR-302c (SEQ.ID.NO.8), and pro-miR-302d (SEQ.ID.NO.9) sequences (13B). After transcription, the sequence of the miR-302 familial cluster (=pri-miR-302) is 5'-AAUUUUUUUC UUCUAAAGUU AUGCCAUUUU GUUUUCUUUC UCCUCAGCUC UAAAUACUCU GAAGUCCAAA GAAGUUGUAU GUUGGGUGGG CUCCCUUCAA CUUUAACAUG GAAGUGCUUU CUGUGACUUU AAAAGUAAGU GCUUCCAUGU UUUAGUAGGA GUGAAUCCAA UUUACUUCUC CAAAAUAGAA CACGCUAACC UCAUUUGAAG GGAUCCCCUU UGCUUUAACA UGGGGGUACC UGCUGUGUGA AACAAAAGUA AGUGCUUCCA UGUUUCAGUG GAGGUGUCUC CAAGCCAGCA CACCUUUUGU UACAAAAUUU UUUUGUUAUU GUGUUUUAAG GUUACUAAGC UUGUUACAGG UUAAAGGAUU CUAACUUUUU CCAAGACUGG GCUCCCCACC ACUUAAACGU GGAUGUACUU GCUUUGAAAC UAAAGAAGUA AGUGCUUCCA UGUUUUGGUG AUGGUAAGUC UUCUUUUUAC AUUUUUAUUA UUUUUUUAGA AAAUAACUUU AUUGUAUUGA CCGCAGCUCA UAUAUUUAAG CUUUAUUUUG UAUUUUUACA UCUGUUAAGG GGCCC CCUCUAC UUUAACAU GGAGGCACUU GCUGUGACAU GACAAAAAUA AGUGCUUCCA UGUUUGAGUG UGGUGGUUCC UACCUAAUCA GCAAUUGAGU UAACGCCCAC ACUGUGUGCA GUUCUUGGCU ACAGGCCAUU ACUGUUGCUA-3' (SEQ.ID.NO.5), while the individual sequences of pro-miR-302a, pro-miR-302b, pro-miR-302c, and pro-miR-302d are as follows: 5'-CCACCACUUA AACGUGGAUG UACUUGCUUU GAAACUAAAG AAGUAAGUGC UUCCAUGUUU UGGUGAUGG-3' (SEQ.ID.NO 0.6), 5'-GCUCCCUUCA ACUUUAACAU GGAAGUGCUU UCUGUGACUU UAAAAGUAAG UGCUUCCAUG UUUUAGUAGG AGU-3' (SEQ.ID.NO.7), 5'-CCUUUGCUUU AACAUGGGGG UAC-CUGCUGU GUGAAACAAA AGUAAGUGCU UCCAUGUUUC AGUGGAGG-3' (SEQ.ID.NO.8), and 5'-CCUCUACUUU AACAUGGAGG CACUUGCUGU GACAUGACAA AAAUAAGUGC UUCCAUGUUU GAGUGUGG-3' (SEQ.ID.NO.9), respectively.

Figure 14:
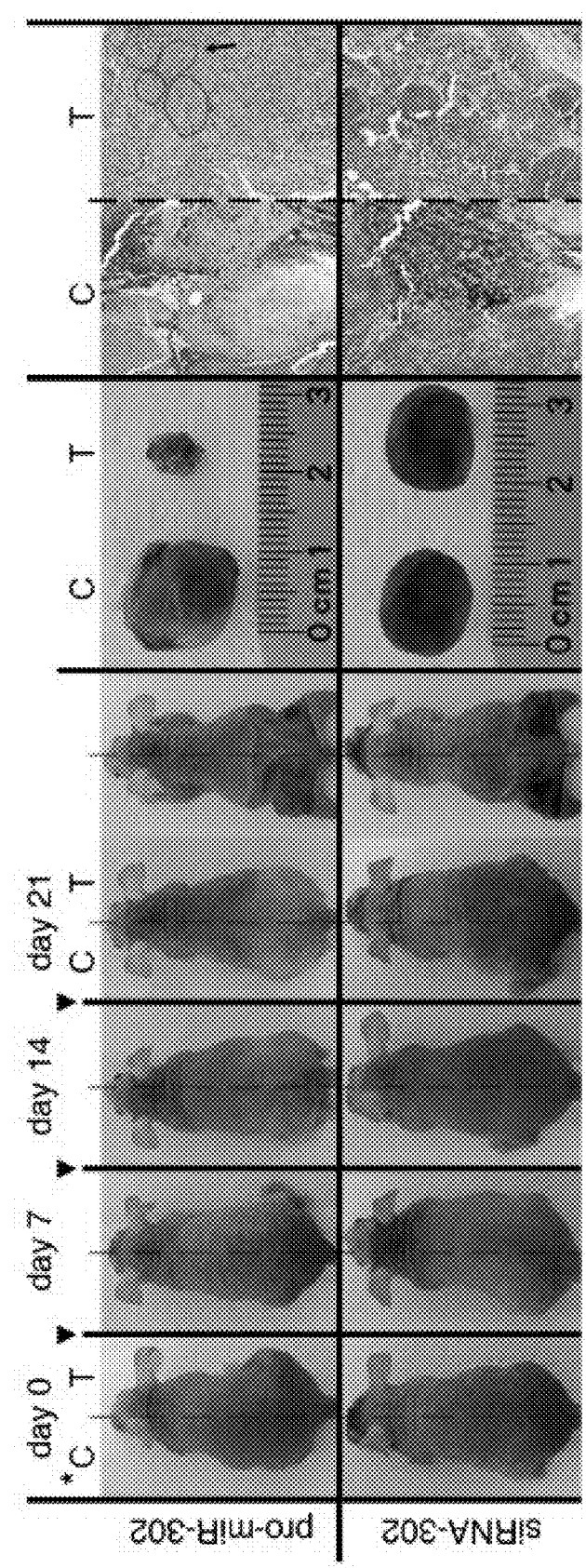

FIG. 14 shows the in vivo therapeutic results of a pre-investigational new drug (pre-IND) trial using pro-miR-302 as an injection drug to treat human liver cancer xenografts in SCID-beige nude mice. Following three treatments (once per week), the pro-miR-302 drug (=pre-miR-302) successfully reduced cancer sizes from 728±328 mm$^3$ (untreated blank control, C) to 75±15 mm$^3$ (pro-mir-302-treated, T), indicating a ~90% reduction rate in the average cancer size!

No significant therapeutic effect was found in the treatments of synthetic siRNA mimics (siRNA-302). Further histological examination (most right) found that normal liver lobule-like structures (circles pointed by a black arrow) were formed only in pro-miR-302-treated cancers but not other treatments or controls, suggesting that a reprogramming mechanism may occur to reset the malignant cancer cell properties back to a relatively normal-like state, called "Cancer Reversion".

Figure 15:
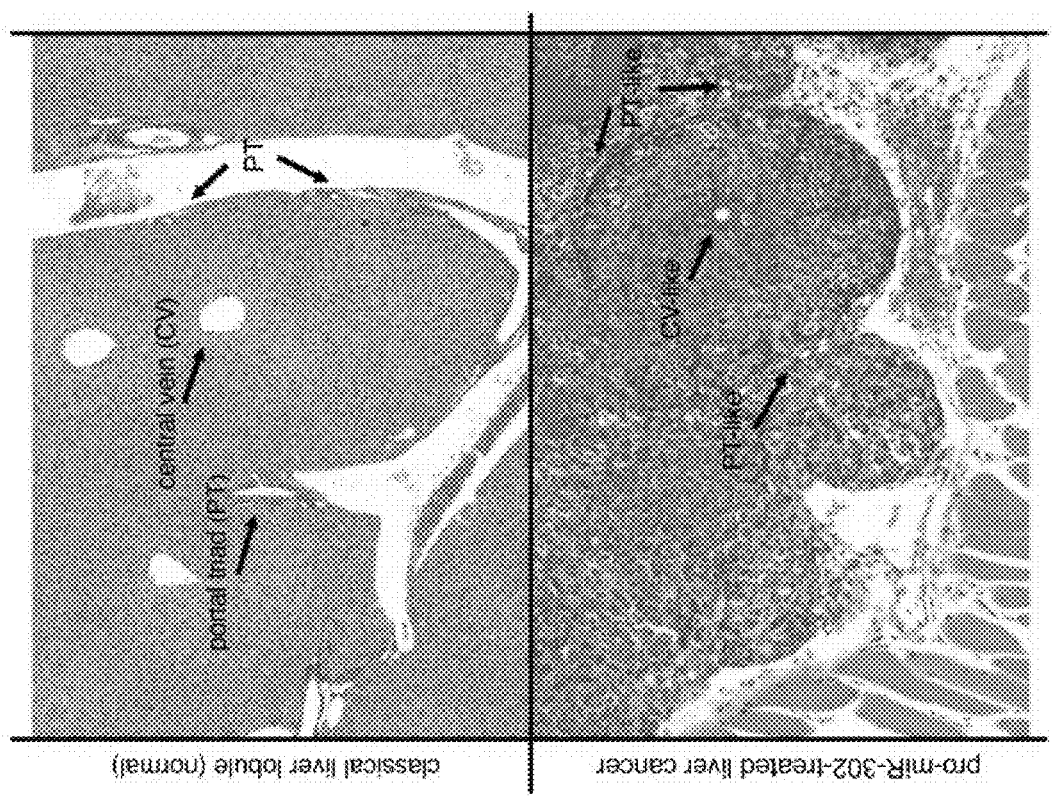

FIG. 15 shows the histological similarity between normal liver tissues and pro-mir-302-treated human liver cancer xenografts in vivo. After three treatments (once per week), the pro-mir-302 drug successfully reprogrammed high-grade (grade IV) human liver cancer grafts to a more benign low-grade (less than grade II) state. Similar to normal liver tissues (top), the treated cancer grafts could form classical liver lobules, containing central vein (CV)-like and portal triad (PT)-like structures (indicated by black arrows). As cancer cells are generally more acidic than normal liver cells, the result of hematoxylin & eosin (H&E) staining shows more purple in cancer cells whereas more red in normal liver cells.

Figure 16:
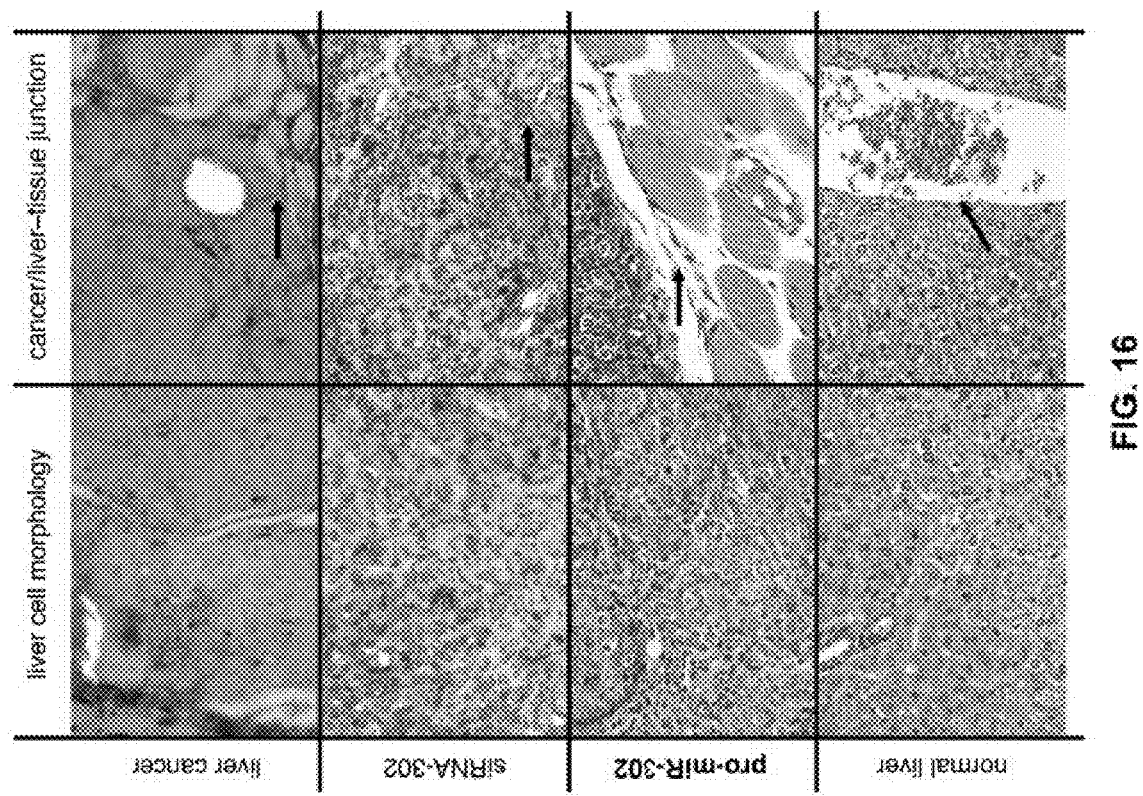

FIG. 16 shows the patho-histological comparison among untreated, siRNA-treated, pro-mir-302-treated human liver cancer grafts and normal liver tissues in SCID-beige nude mice. Without treatment (top), the engrafted human liver cancer aggressively invaded into normal tissues, such as muscles and blood vessels, and formed massive cell-cell and cancer-tissue fusion structures, indicating its malignancy and high metastasis. Treatment of siRNA mimics (siRNA-302) did not significantly reduce the malignancy of the engrafted cancer (upper middle), probably due to the short half-life of siRNA. In contrast, pro-miR-302 treatment not only reprogrammed the engrafted cancer to a relatively normal-like morphology (no fusion) but also greatly inhibited cancer invasion into the surrounding tissues (lower middle). Compared to normal liver tissues (bottom), pro-miR-302-treated cancers formed normal-like lobule structures, gland-like cell arrangements, and clear boundaries between cell-cell and cancer-tissue junctions (black arrows), indicating that these treated cancers have been downgraded to a very benign state.

FIGS. 17A and 17B show comparison of the healing results between untreated (17A) and miR-302-treated (17B) wounds in vivo. The isolated pre-miR-302s (20~400 µg/mL) were formulated with di-/tri-glycylglycerins, a delivery reagent, and antibiotic ointment to form candidate drugs for testing the in-vivo treatments of large 2 cm×2 cm open wounds on pig back skins (n=6 for each group). After ten (10) treatments, the healed wounds were dissected and further made into tissue sections for histological examination under a microscope. The data showed that no or very little scar (scarless) could be seen in the miR-302-treated wounds (17B top, n=6/6), whereas almost all untreated wounds (treated with only antibiotic ointment) contained relatively large scars (17A). Also, a significantly large amount of CD34-positive adult stem cell expansion clusters (labeled by green fluorescent antibodies) were found in the miR-302-treated wounds (17B bottom, n=6/6), but not in untreated control wounds (17A bottom, n=0/6). These results indicate that pre-miR-302 is able to induce CD34-positive adult stem cell expansion and/or regeneration, so as to enhance tissue repairing and regeneration, leading to a very beneficial therapeutic effect on lesions caused by human degenerative diseases, such as Alzheimer's diseases, Parkinson's diseases, osteoporosis, diabetes, and cancers. Such therapeutic effect may also help to reprogram high-grade malignant cancers into low-grade benign or even normal-like tissues, a novel mechanism called "Cancer Reversion" or "Cancer Regression".

Figure 18:
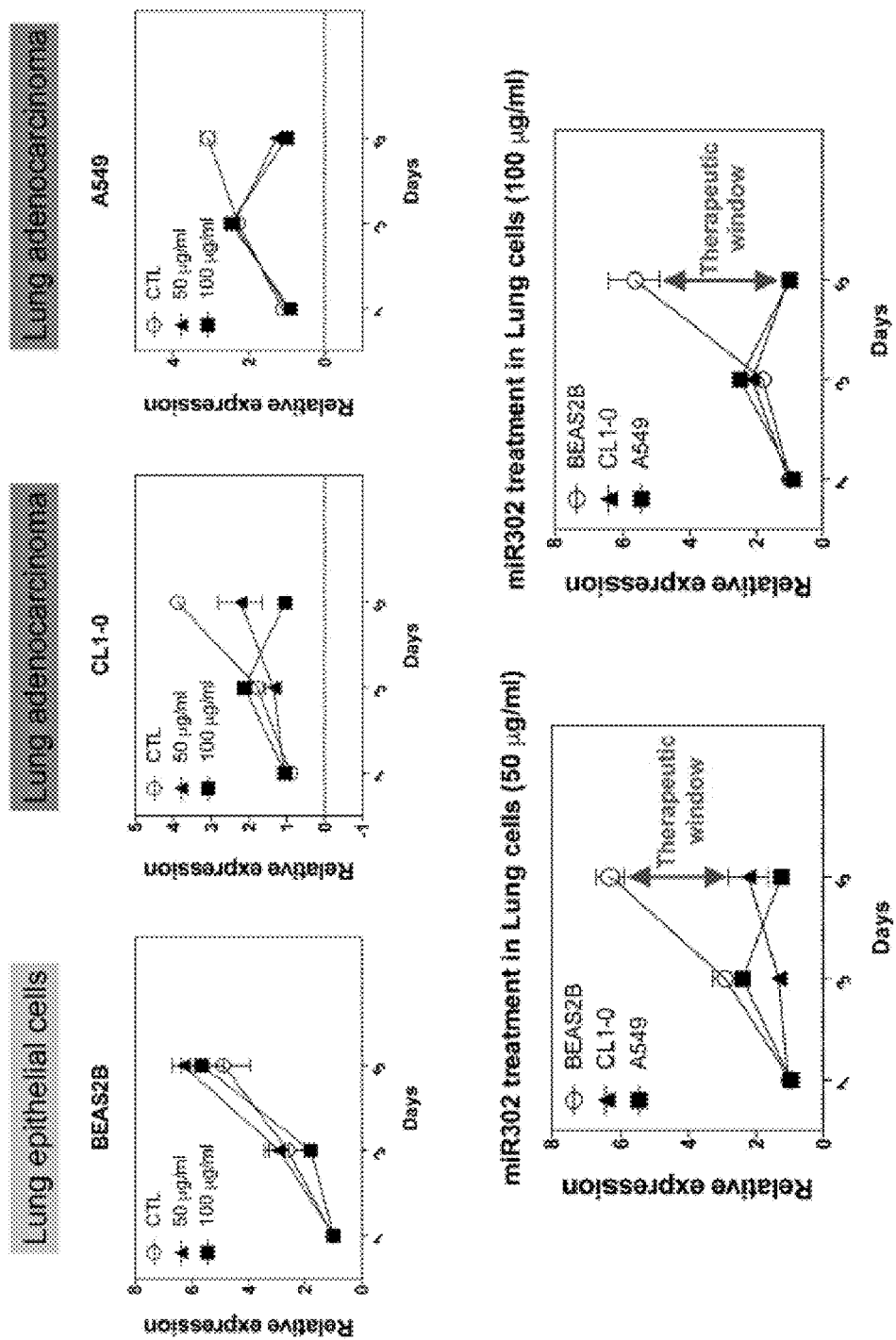

FIG. 18 shows the results of dose-dependent cancer therapy using pro-miR-302 as an anti-cancer drug for treating normal lung epithelial cell line BEAS2B (top left), cancerous lung adenocarcinoma tissue cells isolated from a lung cancer patient CL1-0 (top middle), and lung adenocarcinoma tissue cells isolated from another cancer patient A549 (top right) as well as the dose-dependent therapeutic results of these lung cancers in response to pro-miR-302 treatments at two different concentrations of 50 (bottom left) and 100 (bottom right) microgram (µg)/mL, respectively.

Figure 19A:
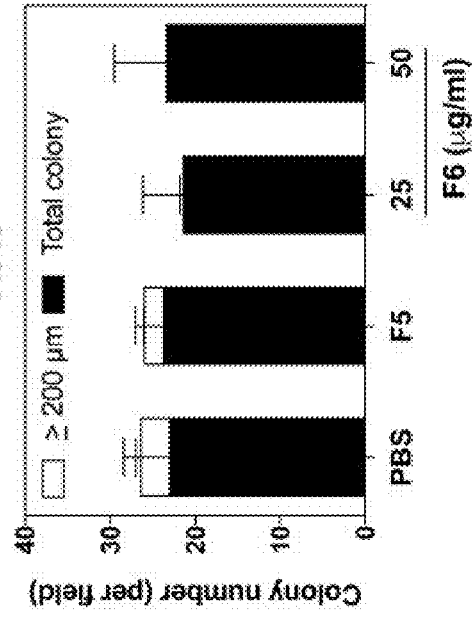
Figure 19B:
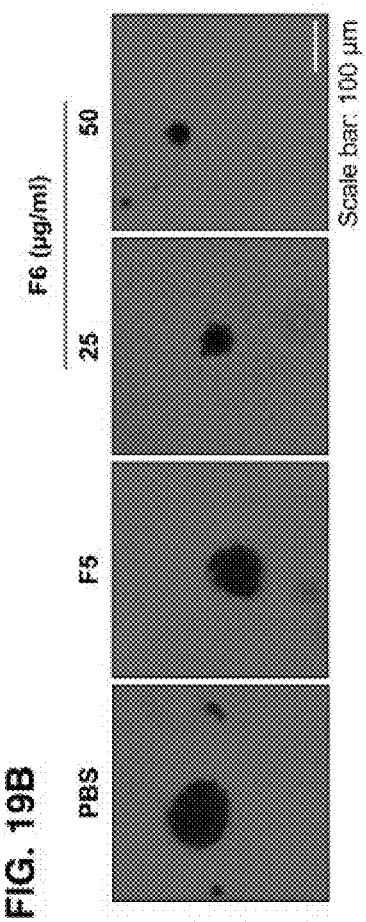

FIGS. 19A and 19B show the therapeutic potency of a formulated pre-miR-302 (F6) drug directed against the growth of malignant lung cancer cells in vitro, using a soft agar colony formation assay. FIG. 19A demonstrated the bar-chart results of the inhibitory effect of F6 on the colony number and size of human malignant lung cancer A 549 cell line. FIG. 19B showed the photos of the average cancer colony sizes before and after different F6 treatments, from left to right: control (original cancers treated with PBS), F5 (treated with the glycylglycerin-based formulation solution only), F6-25 (treated with 25 µg/mL F6), and F6-50 (treated with 50 µg/mL F6), respectively.

FIG. 20 shows the mutation status of several driver genes in a variety of different human lung cancer cell lines and types, including the mutant types of EGFR, p53, and K-ras oncogenes (as shown on the panels to the left of the middle column of pictures of the different cancer cell colonies). The middle column of FIG. 20 shows the pictures of cancer colonies formed by original cancer cells derived from four different human lung cancer cell lines (types) without any treatment, whereas the panels to the right of the middle column of pictures display the inhibitory effect of one F6 treatment (50 µg/mL) on the colony formation of these different lung cancer types, of which the resulting drug potency is categorized into four groups: sensitive (reduced >50% in the average colony size), partial sensitive (reduced 25~50%), partial resistant (reduced <25%), and resistant groups (no effect 0%).

FIGS. 21A and 21B show the time schedule flowchart of treatment frequency (21A) and image taking frequency (21B) of the first animal trial experiments using a formulated pro-miR-302 (=pre-miR-302) drug, called F6, to treat highly malignant and metastatic human lung cancer implants in mice.

Figure 22B:
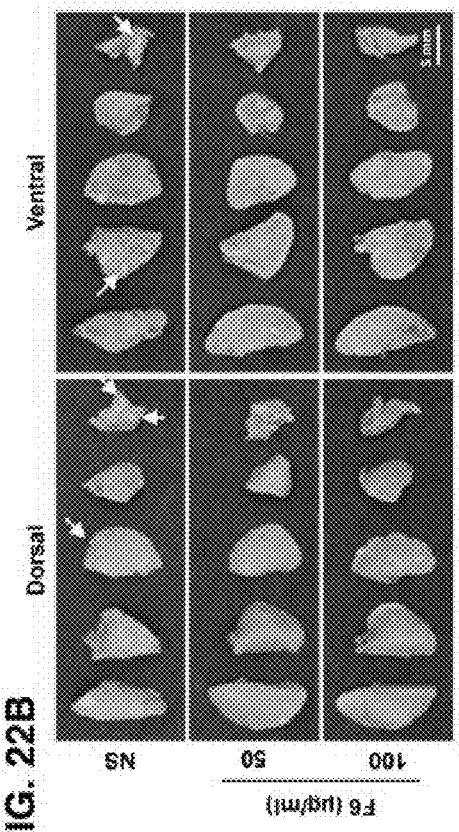
Figure 22A:
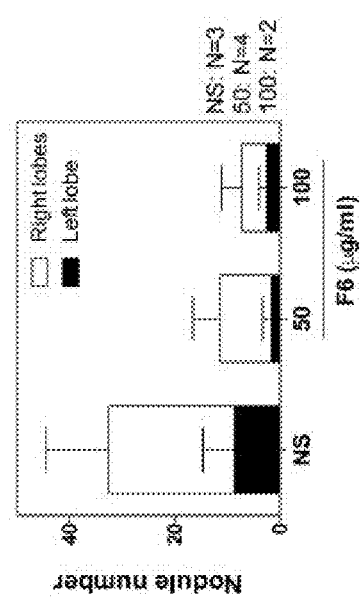
Figure 22C:
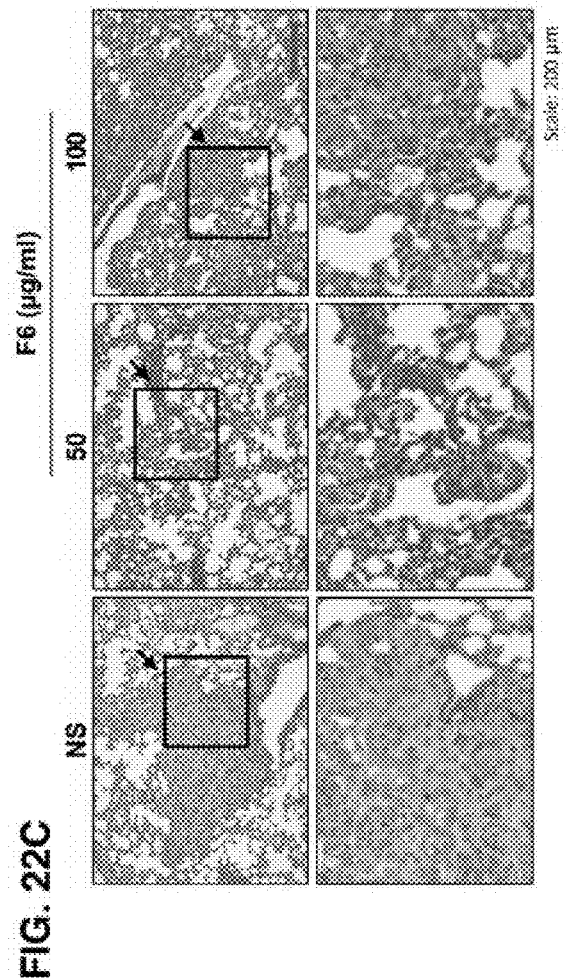

FIGS. 22A, 22B and 22C show the therapeutic results of the first animal trial experiments using a formulated pro-miR-302 (=pre-miR-302) drug, called F6, to treat highly malignant and metastatic human lung cancer implants in mice. FIG. 22A demonstrated the numbers of lung cancer nodules found in different treatment and control groups of mice, and FIG. 22B showed the representative photo pictures of all lung cancer tissues found in both of the treatment and control groups, respectively. FIG. 22C showed the histological examination results of typical lung adenocarcinoma structures (circled and pointed by a black arrow).

FIGS. 23A and 23B show the time schedule flowchart of treatment frequency (23A) and image taking frequency (23B) of the second animal trial experiments using a formulated pre-miR-302 (F6) drug to treat highly malignant and metastatic human NSCLC implants in mice.

Figure 24B:
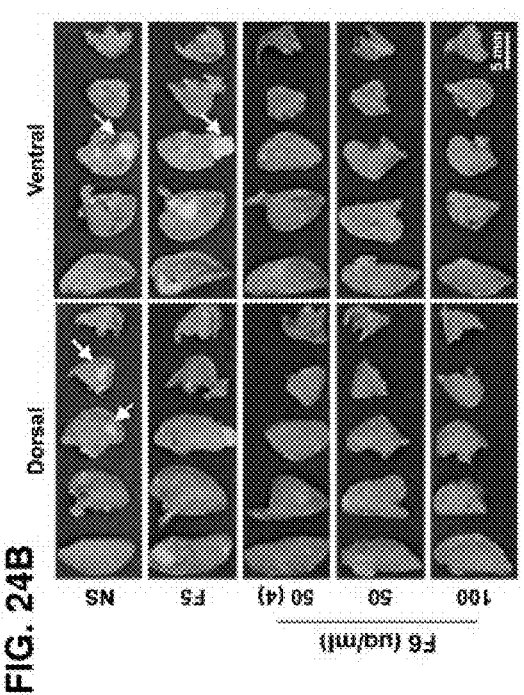
Figure 24A:
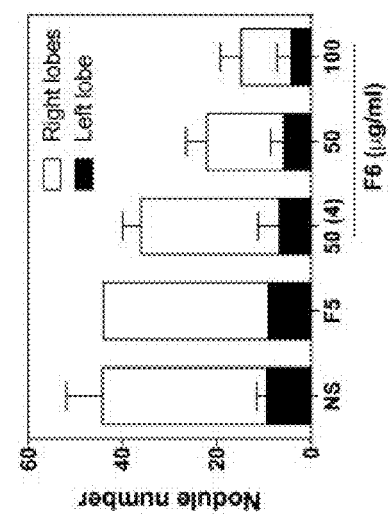
Figure 24C:
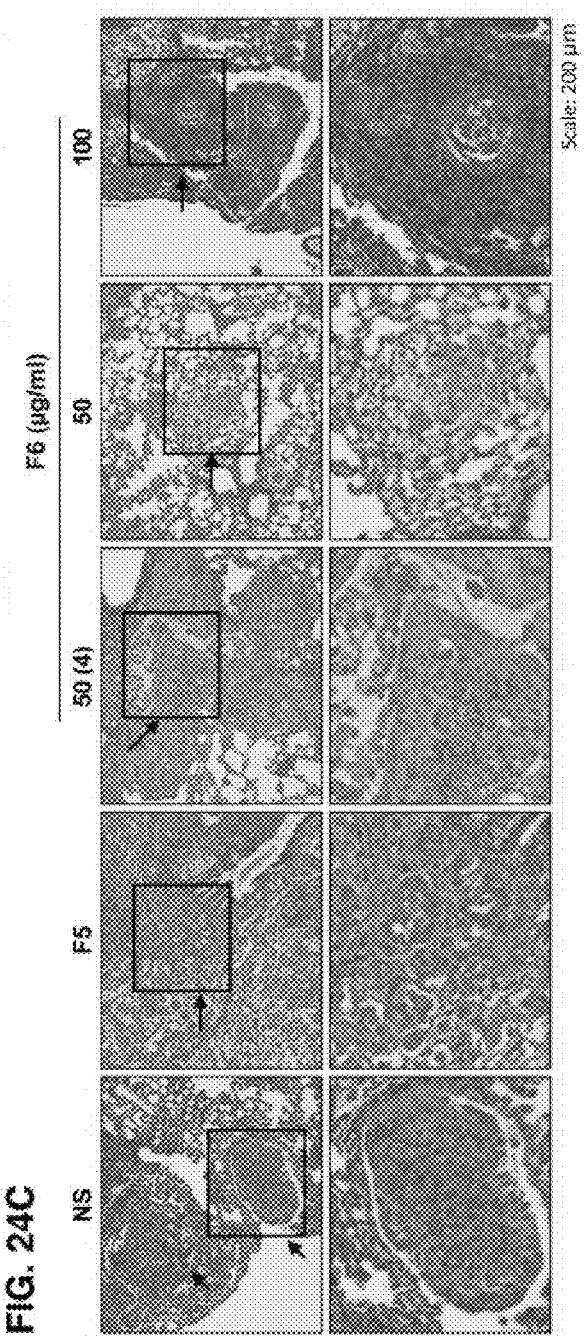

FIGS. 24A, 24B and 24C show the therapeutic results of the second animal trial experiments with a reduced frequency of drug treatments compared to that of the first animal trial, using a formulated pre-miR-302 (F6) drug, to treat highly malignant and metastatic human NSCLC in mice. FIG. 24A demonstrated the numbers of lung cancer nodules found in different treatment and control groups of mice, and FIG. 24B showed the representative photo pictures of all lung cancer tissues found in both of the treatment and control groups, respectively. FIG. 24C showed lymphocyte infiltration, a typical anti-cancer immune response in effect, in the implanted tumors/cancers after the F6 treatments (circled and pointed by a black arrow).

DETAILED DESCRIPTION

In the experimental disclosure which follows, the following abbreviations apply: M (molar); mM (millimolar); μm (micromolar); mol (moles); pmol (picomoles); gm (grams); mg (milligrams); μg (micrograms); ng (nanograms); L (liters); ml (milliliters); μl (microliters); °C. (degrees Centigrade); RNA (ribonucleic acid); DNA (deoxyribonucleic acid); dNTP (deoxyribonucleotide triphosphate); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); ATCC (American Type Culture Collection, Rockville, Md.); hESC (human embryonic stem cells); and iPSC (induced pluripotent stem cells).

Examples

1. Bacterial Cell Culture and Chemical Treatments

Figure 1A:
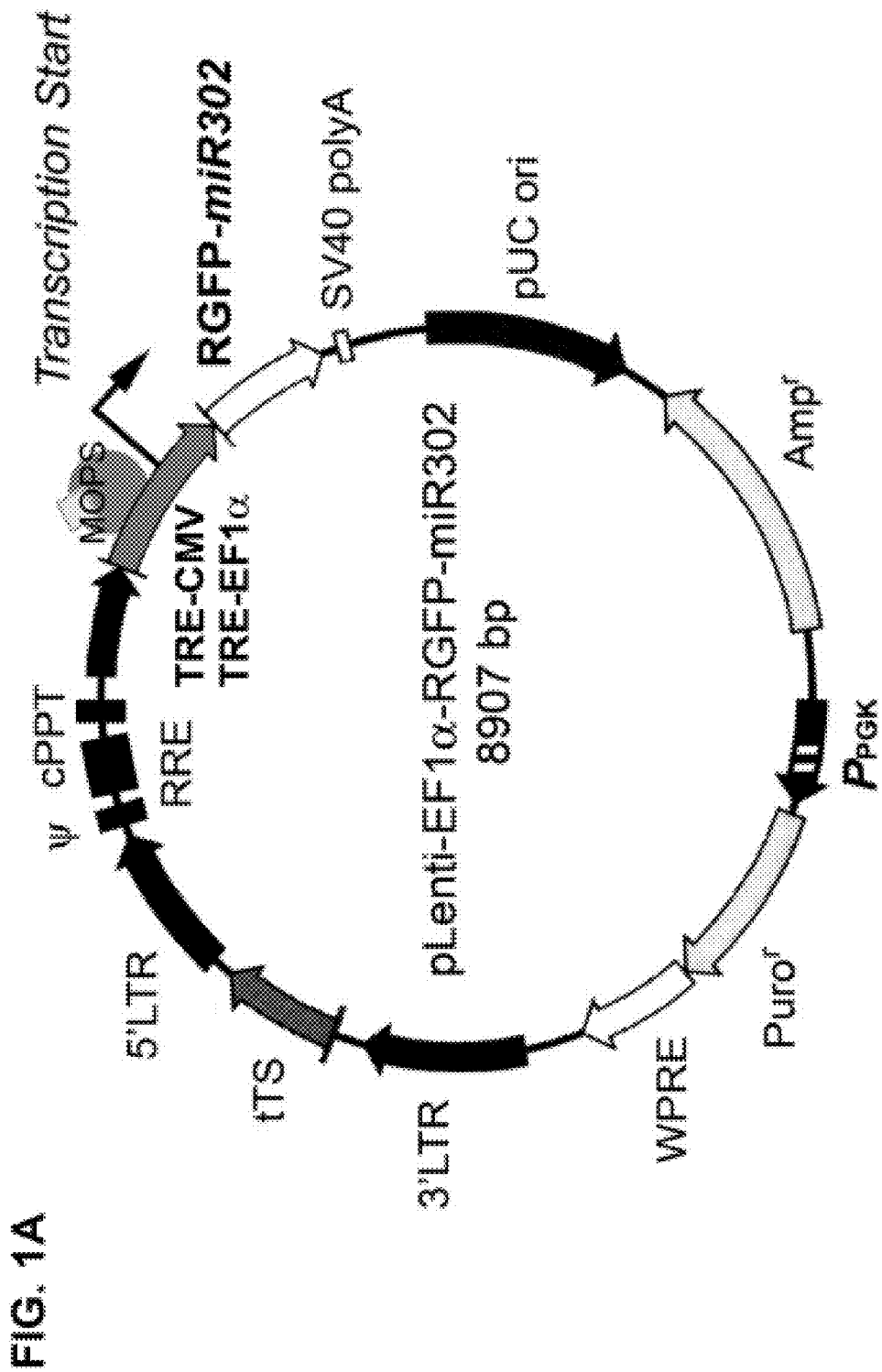
FIGS. 1A and 1B show a eukaryotic promoter-driven expression vector composition (1A) and its expression mechanism (1B) for RNA transcript and/or protein production in prokaryotes. For demonstrating the present invention, a newpLenti-EF1alpha-RGFP-miR302 vector (FIG. 1A) is served as an example composition for transforming *E. coli* DH5alpha competent cells to produce RGFP proteins as well as miR-302s and their precursors (pre-miR-302s) under the stimulation of MOPS, glycerin and/or ethanol. pLenti-EF1alpha-RGFP-miR302 is a lentiviral plasmid vector that is designed by the inventors to contain a gene expression cassette encoding the miR-302 familial cluster sequence (SEQ.ID.NO.5) in the 5'-UTR region of a modified red fluorescent protein (RGFP) gene. The design of pLenti-EF1alpha-RGFP-miR302 is useful for expressing the precursors of many varieties of microRNAs, shRNAs, and siRNAs in both prokaryotes and eukaryotes. According to the disclosed mechanism (1B), it is easy for an ordinary skill person in the art to use any microRNA/shRNA/siRNA in place of miR-302 for inducing eukaryotic promoter-mediated gene expression as described in the present invention. Black arrows indicate the pathways occurring in both prokaryotic and eukaryotic cells, while blank arrows indicate the steps only occurring in the eukaryotic cells.
Figure 1B:
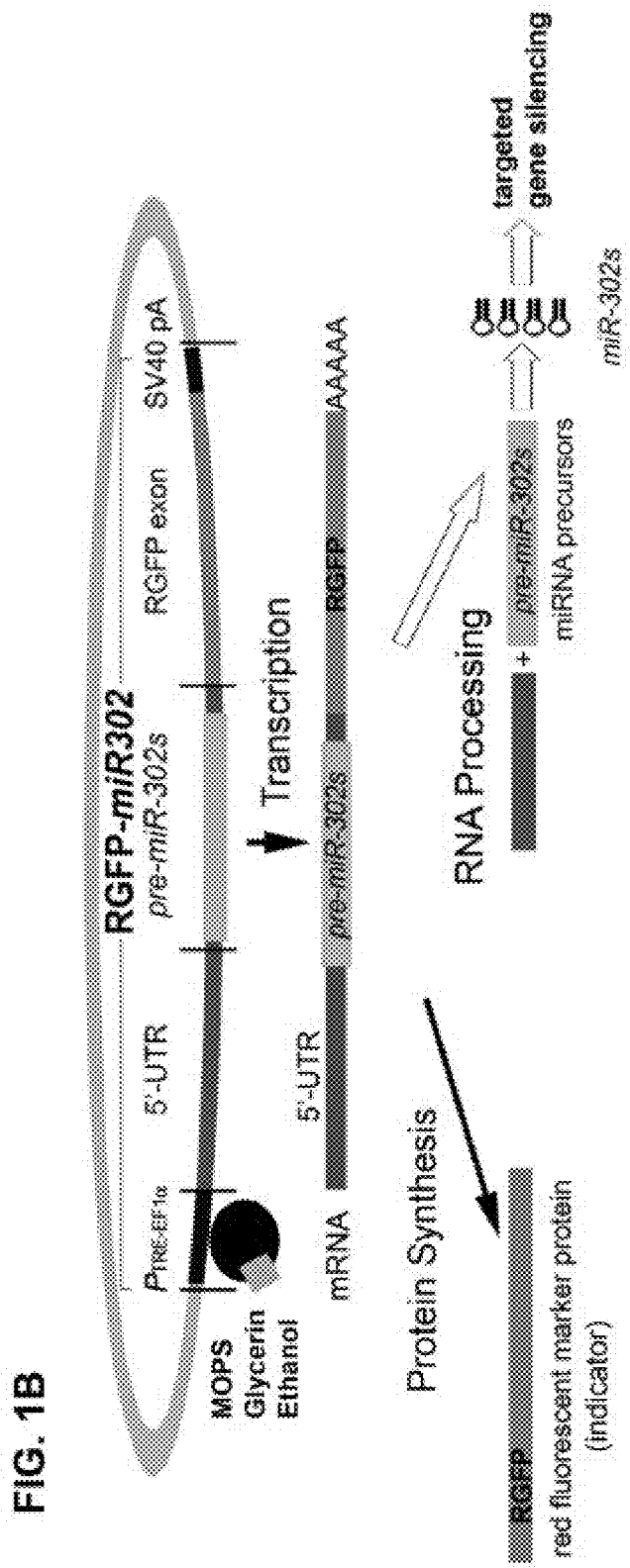
Figure 3:
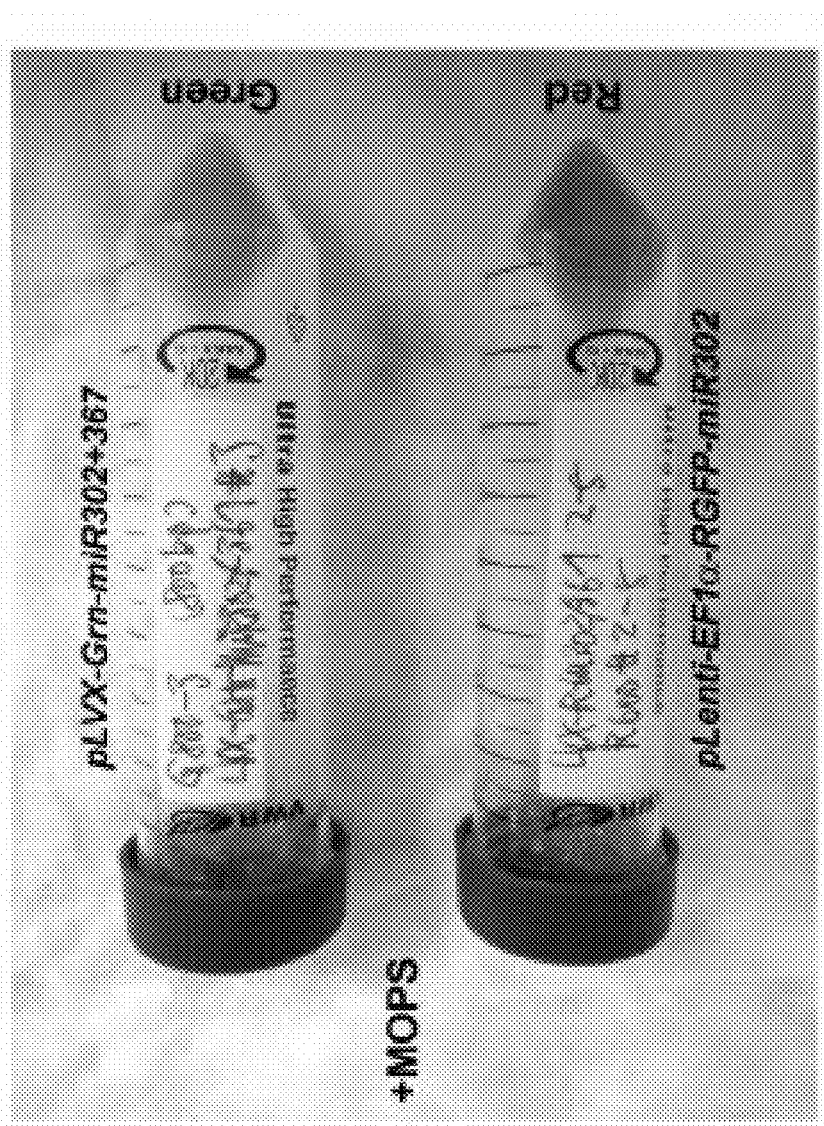
FIG. 3 shows the results of different bacterial pellets after treated with 0.1% (v/v) MOPS. The *E. coli* competent cells have been transformed by either pLVX-Grn-miR302+367 (green) or pLenti-EF1alpha-RGFP-miR302 (red) before the MOPS treatment.
Figure 4:
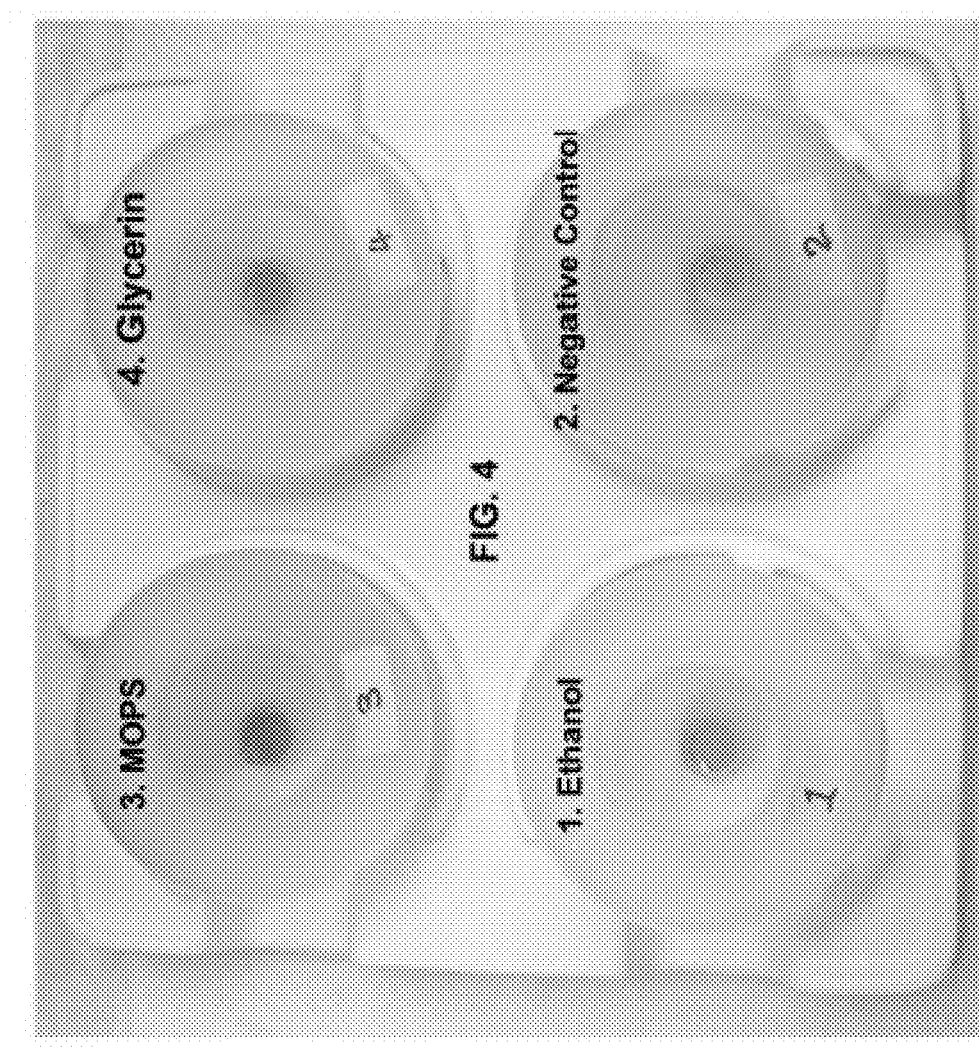
FIG. 4 shows the inducibility of various chemical inducers for inducing pol-2 promoter-driven gene expression in *E. coli* competent cells. Among all chemicals tested, the top three most potent inducers are MOPS, glycerin and ethanol.

*E. coli* DH5alpha competent cells were acquired as a part from the z-competent *E. coli* transformation kit (Zymo Research, Irvine, Calif.) and then transformed by mixing with 5 μg of a pre-made plasmid vector such as pLenti-EF1alpha-RGFP-miR302 or pLVX-Grn-miR302+367. Non-transformed cells were normally grown in Luria-Bertani (LB) broth supplemented with 10 mM $MgSO_4$ and 0.2 mM glucose at 37° C. with frequent agitation at 170 rpm, whereas the transformed cells are cultivated in the above LB broth further supplemented with additional 100 μg/ml ampicillin. For chemical induction, 0.5 to 2 ml of MOPS, glycerin and/or ethanol, respectively or in combination, was added into 1 litter LB broth supplemented with 10 mM $MgSO_4$ and 0.2 mM glucose in the presence of 100 μg/ml ampicillin. For negative control, the transformed cells were cultivated in the above ampicillin-supplemented LB broth but without adding any chemical inducer. The results are shown in FIGS. 2-4.

2. Human Cell Culture and MicroRNA Transfection

Human liver cancer cell line HepG2 was obtained from ATCC and maintained according to manufacturer's suggestions. For transfection, 15 μg of pre-miR-302 was dissolved in 1 ml of fresh RPMI medium and mixed with 50 μl of X-tremeGENE HP DNA transfection reagent (Roche, Indianapolis, Ind.). After 10 min incubation, the mixture is added into a 100-mm cell culture dish containing 50° ~60% confluency of HepG2. The medium was refreshed 12 to 18 hours later. After these transfected cells formed sphere-like iPSC colonies, the medium was changed to a knockout DMEM/F-12 medium (Invitrogen) supplemented with 20% knockout serum, 1% MEM nonessential amino acids, 100 μM β-mercaptoethanol, 1 mM GlutaMax, 1 mM sodium pyruvate, 10 ng/ml bFGF, 10 ng/ml FGF-4, 5 ng/ml LIF, 100 IU/ml penicillin/100 μg/ml streptomycin, 0.1 μM A83-01, and 0.1 μM valproic acid (Stemgent, San Diego, Calif.), and the cells were cultivated at 37° C. under 5% $CO_2$. The result is shown in FIG. 9.

3. Protein Extraction and Western Blot Analysis

Cells ($10^6$) were lysed with a CelLytic-M lysis/extraction reagent (Sigma) supplemented with protease inhibitors, Leupeptin, TLCK, TAME and PMSF, following the manufacturer's suggestion. Lysates were centrifuged at 12,000 rpm for 20 min at 4° C. and the supernatant was recovered. Protein concentrations were measured using an improved SOFTmax protein assay package on an E-max microplate reader (Molecular Devices, Calif.). Each 30 μg of cell lysate was added to SDS-PAGE sample buffer under reducing (+50 mM DTT) and non-reducing (no DTT) conditions, and boiled for 3 min before loading onto a 6~8% polyacylamide gel. Proteins were resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hours at room temperature. Then, a primary antibody was applied to the reagent and incubated the mixture at 4° C. Primary antibodies included Oct3/4 (Santa Cruz Biotechnology, Santa Cruz, Calif.), RuvB (Santa Cruz) and RGFP (Clontech). After overnight, the membrane was rinsed three times with TBS-T and then exposed to goat anti-mouse IgG conjugated secondary antibody to Alexa Fluor 680 reactive dye (1:2,000; Invitrogen—Molecular Probes), for 1 hour at the room temperature. After three additional TBS-T rinses, fluorescent scanning of the immunoblot and image analysis was conducted using Li-Cor Odyssey Infrared Imager and Odyssey Software v.10 (Li-Cor). The results are shown in FIG. 5.

4. RNA Extraction and Northern Blot Analysis

Total RNAs (10 μg) were isolated with a mirVana™ miRNA isolation kit (Ambion, Austin, Tex.), fractionated by either 15% TBE-urea polyacrylamide gel or 3.5% low melting point agarose gel electrophoresis, and electroblotted onto a nylon membrane. Detection of miR-302s and the related pre-miR-302s was performed with a [LNA]-DNA probe (5'-[TCACTGAAAC] ATGGAAGCAC TTA-3') (SEQ.ID.NO.10) probe. The probe has been purified by high-performance liquid chromatography (HPLC) and tail-labeled with terminal transferase (20 units) for 20 min in the presence of [$^{32}$P]-dATP (>3000 Ci/mM, Amersham International, Arlington Heights, Ill.). The results are shown in FIG. 6.

5. Plasmid Amplification and Plasmid DNA/Total RNA Extraction

*E. coli* DH5alpha competent cells after transformation (from Example 1) were cultivated in LB broth supplemented with 10 mM $MgSO_4$ and 0.2 mM glucose at 37° C. with frequent agitation at 170 rpm. For inducing eukaryotic promoter-driven RNA transcription, 0.5 to 2 ml of MOPS, glycerin, and/or ethanol was added into every 1 litter of LB broth for propagating the transformed cells overnight. The amplified plasmid DNAs and expressed mRNAs/microRNAs in the transformed cells were isolated using a HiSpeed plasmid purification kit (Qiagen, Valencia, Calif.), following the manufacturer's protocol but with a minor modification that RNase A was not added into the P1 buffer. After that, the final extracted products containing both plasmids and mRNAs/microRNAs were dissolved in DFPC-treated ddH₂O and stored at −80° C. before use. For purifying only the amplified plasmid vectors, RNase A was added into the P1 buffer and the extraction procedure was performed following the manufacturer's protocol.

6. MicroRNA and Pre-miRNA Isolation/Purification

For purifying microRNAs and pre-miRNAs, the total RNAs isolated from Example 5 were further extracted using a mirVana™ miRNA isolation kit (Ambion, Austin, Tex.), following the manufacturer's protocol. The final products so obtained were dissolved in DEPC-treated ddH₂O and stored at −80° C. before use. Because bacterial RNAs are naturally degraded very fast (within a few hours) whereas eukaryotic hairpin-like microRNA precursors (pre-miRNAs and pri-miRNAs) remain largely stable at 4° C. (half-life up to 3-4 days), we can use this half-life difference to acquire relatively pure pri-/pre-miRNAs for other applications. For example, the pre-miR-302s so obtained can be used to reprogram somatic cells to hESC-like iPSCs, as shown in FIG. 9.

7. Immunostaining Assay

Embedding, sectioning and immunostaining tissue samples were performed as previously reported (Lin et al., 2008). Primary antibodies include Oct4 (Santa Cruz) and RGFP (Clontech, Palo Alto, Calif.). Fluorescent dye-labeled goat anti-rabbit or horse anti-mouse antibody was used as the secondary antibody (Invitrogen—Molecular Probes, Carlsbad, Calif.). Positive results were examined and analyzed at 100× or 200× magnification under a fluorescent 80i microscopic quantitation system with a Metamorph imaging program (Nikon). The result is shown in FIG. 7.

8. Bisulfite DNA Sequencing

Genomic DNAs were isolated from ~2,000,000 cells using a DNA isolation kit (Roche) and 1 µg of the isolated DNAs was further treated with bisulfite (CpGenome DNA modification kit, Chemicon, Temecula, Calif.), following the manufacturers' suggestion. The bisulfite treatment converted all unmethylated cytosine to uracil, while methylated cytosine remained as cytosine. For bisulfite DNA sequencing, we amplified the promoter region of the Oct4 gene with PCR primers: 5'-GAGGCTGGAG CAGAAGGATT GCTTTGG-3' (SEQ.ID.NO.11) and 5'-CCCTCCTGAC CCATCACCTC CACCACC-3' (SEQ.ID.NO.12). For PCR, the bisulfite-modified DNAs (50 ng) were mixed with the primers (total 100 pmol) in 1×PCR buffer, heated to 94° C. for 2 min, and immediately cooled on ice. Next, 25 cycles of PCR were performed as follows: 94° C. for 1 min and 70° C. for 3 min, using an Expand High Fidelity PCR kit (Roche). The PCR product with a correct size was further fractionized by 3% agarose gel electrophoresis, purified by a gel extraction filter (Qiagen), and then used in DNA sequencing. After that, a detailed profile of DNA methylation sites was generated by comparing the unchanged cytosine in the converted DNA sequence to the unconverted one, as shown in FIG. 8.

9. DNA-Density Flow Cytometry

Cells were trypsinized, pelleted and fixed by re-suspension in 1 ml of pre-chilled 70% methanol in PBS for 1 hour at −20° C. The cells were pelleted and washed once with 1 ml of PBS and then pelleted again and resuspended in 1 ml of 1 mg/ml propidium iodide, 0.5 µg/ml RNase in PBS for 30 min at 37° C. After that, about 15,000 cells were analyzed on a BD FACSCalibur (San Jose, Calif.). Cell doublets were excluded by plotting pulse width versus pulse area and gating on the single cells. The collected data were analyzed using the software package Flowjo using the "Watson Pragmatic" algorithm. The result was shown in the top panels of FIG. 9.

10. MicroRNA (miRNA) Microarray Analysis

At about 70% confluency, small RNAs from each cell culture were isolated, using the mirVana™ miRNA isolation kit (Ambion). The purity and quantity of the isolated small RNAs were assessed, using 1% formaldehyde-agarose gel electrophoresis and spectrophotometer measurement (Bio-Rad), and then immediately frozen in dry ice and submitted to LC Sciences (San Diego, Calif.) for miRNA microarray analyses. Each microarray chip was hybridized a single sample labeled with either Cy3 or Cy5 or a pair of samples labeled with Cy3 and Cy5, respectively. Background subtraction and normalization were performed as manufacturer's suggestions. For a dual sample assay, a p-value calculation was performed and a list of differentially expressed transcripts more than 3-fold (yellow-red signals) was produced. The final microarray results were shown in FIGS. 11A and 11B, and the list of differentially expressed microRNAs was shown in FIG. 12, which compared the small RNAs extracted from blank *E. coli* cell lysates (Group 1) to those extracted from pLenti-EF1alpha-RGFP-miR302-transformed cell lysates (Group 2).

11. In Vivo Liver Cancer Therapy Trials

Xenografting human liver cancers into immunocompromised SCID-beige mice is a valid animal model for studying liver cancer metastasis and therapy. To establish this model, we mixed 5 million human hepatocarcinoma (HepG2) cells with 100 µL of matrix gel and subcutaneously engrafted the mixture into each flank of the mouse hind limbs, respectively. As a result, both sides of the mouse hind limbs were subjected to approximately the same amount of cancer cell engraftment. Cancers were observed about two weeks post-engraftment and sized about 15.6±8 mm³ in average (starting cancer size before treatment). For each mouse, we selected the side with a larger cancer as the treatment group and the other smaller one as the control group. Since the same mouse was treated with a blank formulation reagent (negative control) in one side and the formulated drug (pro-mir-302) in the other side, the results so obtained can minimize any possible variation due to individual differences.

To deliver pro-mir-302 into the targeted cancer regions in vivo, we contracted a professional formulation company, Latitude (San Diego, Calif.), to liposomally encapsulate pro-miR-302s into 160~200 nm-diameter nanoparticles. These pro-miR-302-containing nanoparticles have been tested to be almost 100% stable at room temperature for over two weeks and at 4° C. for over one month, whereas other synthetic siRNA mimics (siRNA-302) were all quickly degraded over 50% within 3 to 5 days under the same conditions, indicating that pro-miRNA rather than siRNA is stable enough to be used as a drug for therapy. For toxicity assay, we have further injected maximally 300 µL of the formulated pro-miR-302 (1 mg/mL) into the mouse tail vein (n=8), respectively, and observed no detectable side effect in all tested mice over six months. In general, non-modified ribonucleic acids are relatively not immunogenic and can be easily metabolized by tissue cells, rendering a safe tool for in vivo therapy.

For testing drug potency, we subcutaneously injected 200 µL of the formulated pro-mir-302 in one side and 200 µL of the blank formulation reagent in the other side of the mice, respectively, and continued the same injection pattern for three times (one injection per week). The drug and reagent were applied to the surrounding region of the cancer site and absorbed by the cancer and its surrounding tissues within 18 hours. Samples were collected one week after the third injection. Hearts, livers, kidneys and the engrafted cancers were removed for further histological examination. Tumor formation was monitored by palpation and tumor volume was calculated using the formula (length×width)/2. Tumor lesions were counted, dissected, weighed, and subjected to histological examination using H&E and immunostaining assays. Histological examination showed no detectable tissue lesions in heart, liver, and kidney. The results were shown in FIGS. 14, 15 and 16.

12. In Vivo Wound Healing Trials

In this case, the glycylglycerin-encapsulated pre-miR-302s were formulated with a cream-based antibiotic ointment for in-vivo treatments. As miR-302 is the most abundant ESC-specific miRNA species in human ESCs and iPSCs, we have proposed that the somatic cell reprogramming function of miR-302 may be able to induce and/or maintain adult stem cell renewal as well, so as to facilitate the processes of tissue repairing and regeneration in vivo. To test this theory, pig skin wounds were generated by scalpel dissection and sized approximately twi centimeter square (2 $cm^2$). The pre-prepared ointments (0.5 mL) with or without pre-miR-302s (5 mg/mL) were evenly applied on the wounds, respectively, and covered the whole wounded areas, and then further sealed by liquid bandage. The treatments were applied on days 0, 1, 2, 3, 4, 5, 7, 9, 11, 14 and 17. Photos of each wound were taken with Sony DSC-H9 camera on days 0, 1, 2, 3, 4, 5, 7, 9, 11, 14, 17 and 20. The area of each wound at each time point was determined using the Image Pro Plus 7.0 imaging software. Percentage of wound healing or closure at each treatment time point was calculated according to the formula: (day 0 wound area–day N wound area)/day 0 wound area×100. At final, tissue samples were collected from each wound and soaked in 10% (v/v) formalin solution before being used for preparing histological sections for H&E staining. The results of this animal trial demonstrated that miR-302 treatments significantly enhanced the speed of wound healing over twice faster than other miR-434 treatments and blank controls. Moreover, seventeen (17) days after treatments, miR-302-treated wound areas left less or almost no scar (n=6/6), whereas other treatments and controls resulted in relatively large scars. To further measure the miRNA penetration rate in skins, we had isolated total RNAs from the biopsies of the newly healed tissues and then run quantitative reverse transcription-polymerase chain reaction (qRT-PCR) assays with a set of miR-302a-specific primers to confirm that glycylglycerin-encapsulated pre-miR-302s were successfully delivered and processed into mature miR-302 in the treated tissues in vivo.

13. In Vitro Lung Cancer Sensitivity to Drug Tests

The dose-dependent tumor suppression effect of a glycylglycerin-encapsulated pre-miR-302/pro-miRNA drug (or called formula #6; F6) on the growth of different lung cancer cell types was tested using various pre-miR-302 concentrations ranged from 0 to 200 µg/mL, preferably between 25~100 µg/mL (FIG. 18). In order to further test the F6 drug potency against the growth of malignant lung cancer cells, a soft agar colony formation assay was performed, as shown in FIGS. 19A and 19B. Both of the growth and colony formation abilities of a typical human malignant lung cancer cell line A549 were found to be significantly inhibited after one F6 treatment (either 25 or 50 µg/mL), especially in the population of large size colonies (diameter ≥200 µm). In addition, FIG. 20 further demonstrated the mutation status of several driver oncogenes in a variety of different human lung cancer cell types, including the status of mutated EGFR, p53, and K-ras oncogenes. The middle column of FIG. 20 shows the pictures of cancer colonies formed by original cancer cells of four different human malignant/metastatic lung cancer cell lines (types) without any treatment, whereas the panels to the right of the middle column display the inhibitory effect of one F6 treatment (50 µg/mL) on the colony formation of these lung cancer types, of which the resulting drug potency in these cancer cell types was categorized into four groups: sensitive (reduced >50% in the average colony size), partial sensitive (reduced 25~50%), partial resistant (reduced <25%), and resistant groups (0%).

14. In Vivo Lung Cancer Therapy Trials

After understanding the potency of our formulated pre-miR-302 drug (F6) on different human lung cancer cell types, we further analyzed its in-vivo therapeutic potency using an orthotopic lung cancer mouse model. FIGS. 21A and 21B showed the time schedule flowchart of F6 treatment frequency and image taking frequency used in an in-vivo bio-imaging system (IVIS). For orthotopic tumor implantation assays, A549-Luci lung cancer cells ($1*10^5$ cells in 20 µl PBS containing 10 ng Matrigel) were injected into the pleural cavity of 6-week-old NOD SCID mice (n=9 in treatment groups and n=3 in control group). A bio-imaging study with luciferase image observation indicated that these implanted mice developed many lung metastasis nodules four (4) weeks after implantation. After that, mice were treated with F6 twice per week via tail vein injection until sacrifice (FIG. 21A). On day-14 post-implantation, mice were divided into three groups: normal saline (NS), and treatments of either 50 or 100 µg/mL of F6, as shown in the imaging results of IVIS (FIG. 21B). The volume of F6 solution used was calculated based on the ratio of body weight and total blood volume in order to keep the same F6 concentration treated in the same group of tested mice. Luciferase signals were observed and measured once per week. In the end, mice were sacrificed 42 days after the first F6 treatment. Major organs such as lung, live, spleen, and kidneys were collected and fixed by 10% formalin, and then the resulting lung nodules were counted using gross and microscopic examination. The number of mice used for the experiments was based on the goal of having 98% power to detect a 2-fold between-group difference in nodule number at $P<0.05$.

In animal trials using in-vivo orthotopic lung cancer assays (FIGS. 22A-22C), we injected lung cancer cells in the left pleural cavity of each tested mouse to observe the lung to lung metastases. As a result, the cancer nodules found in the right lobes indicated the metastasis of lung cancers from the primary cancer implant side in the left lobe. FIG. 22A demonstrated the numbers of lung cancer nodules in different experimental and control groups, and FIG. 22B showed the representative photo pictures. In FIG. 22A, the black bar illustrated the nodules found in left lobe, and the white bar showed the nodules found in right lobes. As a result shown in FIGS. 22A and 22B, the nodule numbers in both treatment groups (50 and 100 μg/ml) were significantly decreased in both left and right lobes of lung. Further histological examination (FIG. 22C) was also performed to observe typical lung adenocarcinoma structures (circled and pointed by a black arrow) in all groups In order to further evaluate the strong therapeutic effects of the F6 drug on metastatic lung adenocarcinoma, we reduced the treatment frequency of F6 solution in the in-vivo orthotopic lung cancer model (n=11 for both treatment groups and n=5 for control group). As shown in FIGS. 23A and 23B, in this repeated animal trials, mice were treated with F6 via tail vein injection twice per week during the week 3 and 4 and then once a week after week 5 until sacrifice. The applied dosage of F6 was calculated based on the ratio of body weight and total blood volume in order to keep the same F6 concentration treated in all tested mice. Luciferase signals were observed and measured once per week. In the end, mice were sacrificed on day-42 post-treatment. To assess the acute toxicity effects of the pre-miR-302 drug, the mice of one tested group were treated only four times of F6 during the week 3 and 4, which was labeled as the 50 (4) group (FIG. 23B). Furthermore, we also tested the toxicity of glycylglycerin only formula in this in-vivo mouse model to rule out any possible toxicity interference of the delivery formulation agent (F5), which actually presented neither toxicity nor any significant effect on the cancer cells.

15. Statistic Analysis

Any change over 75% of signal intensity in the analyses of immunostaining, western blotting and northern blotting was considered as a positive result, which in turn is analyzed and presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ was considered significant. All p values were determined from two-tailed tests.

REFERENCES

1. Lin S L, Chang D, Chang-Lin S, Lin C H, Wu D T S, Chen D T, and Ying S Y. (2008) Mir-302 reprograms human skin cancer cells into a pluripotent ES-cell-like state. *RNA* 14, 2115-2124.
2. Lin S L and Ying S Y. (2008) Role of mir-302 microRNA family in stem cell pluripotency and renewal. Ying S Y. (Ed.) *Current Perspectives in MicroRNAs*. Springer Publishers press, New York, pp 167-185.
3. Lin S L, Chang D, Ying S Y, Leu D and Wu D T S. (2010) MicroRNA miR-302 inhibits the tumorigenecity of human pluripotent stem cells by coordinate suppression of CDK2 and CDK4/6 cell cycle pathways. *Cancer Res.* 70, 9473-9482.
4. Lin S L, Chang D, Lin C H, Ying S Y, Leu D and Wu D T S. (2011) Regulation of somatic cell reprogramming through inducible mir-302 expression. *Nucleic Acids Res.* 39, 1054-1065.
5. Simonsson S and Gurdon J. (2004) DNA demethylation is necessary for the epigenetic reprogramming of somatic cell nuclei. *Nat Cell Biol.* 6, 984-990.
6. Takahashi et al. (2006). Induction of pluripotent stem cells from mouse embryonic and adult fibroblast cultures by defined factors. *Cell* 126, 663-676.
7. Wang et al. (2008). Embryonic stem cell-specific microRNAs regulate the G1-S transition and promote rapid proliferation. *Nat. Genet.* 40, 1478-1483.
8. Wernig et al. (2007). In vitro reprogramming of fibroblasts into a pluripotent ES-cell-like state. *Nature* 448, 318-324.
9. Yu et al. (2007). Induced pluripotent stem cell lines derived from human somatic cells. *Science* 318, 1917-1920.
10. McDowell et al., (1994) Determination of intrinsic transcription termination efficiency by RNA polymerase elongation rate. *Science* 266, 822-825.
11. U.S. Pat. Nos. 9,394,538, 9,399,773, and 9,422,559 to Lin et al.
12. U.S. Pat. No. 7,959,926 to Buechler.
13. U.S. Pat. No. 7,968,311 to Mehta.
14. European Patent No. FP 2198025 to Lin.
15. U.S. patent application Ser. No. 12/149,725 to Lin.
16. U.S. patent application Ser. No. 12/318,806 to Lin.
17. U.S. patent application Ser. No. 13/572,263 to Lin.

What is claimed is:

1. A method for treating human lung cancer using recombinant hairpin-like microRNA precursors (pre-miRNA), comprising:
   (a) providing at least a hairpin-like pre-miRNA containing SEQ.ID.NO.3; and
   (b) contacting said pre-miRNA of (a) with a cancer tissue subject containing at least a human lung cancer cell, so as to activate the anti-cancer effects of said pre-miRNA of (a) on the lung cancer cells of said cancer tissue subject of (b).

2. The method as defined in claim 1, wherein said pre-miRNA containing SEQ.ID.NO.3 is SEQ.ID.NO.6, SEQ.ID.NO.7, SEQ.ID.NO.8, or SEQ.ID.NO.9, or a combination thereof.

3. The method as defined in claim 1, wherein said pre-miRNA containing SEQ.ID.NO.3 is a precursor of miR-302a, miR-302b, miR-302c, or miR-302d, or a combination thereof.

4. The method as defined in claim 1, further comprising processing said pre-miRNA containing SEQ.ID.NO.3 in the human lung cancer cells into miR-302a, miR-302b, miR-302c, or miR-302d, or a combination thereof.

5. The method as defined in claim 1, further comprising producing said pre-miRNA by eukaryotic promoter-driven RNA transcription in prokaryotic cells.

6. The method as defined in claim 5, wherein producing comprises using a gene expression cassette located in a plasmid vector as the DNA sequence required for inducing said eukaryotic promoter-driven RNA transcription.

7. The method as defined in claim 6, wherein said gene expression cassette encodes a sequence of SEQ.ID.NO.5.

8. The method as defined in claim 6, wherein said plasmid vector is a pLenti-EF1alpha-RGFP-miR302 vector containing either a cytomegaloviral CMV or mammalian EF1alpha promoter, or both.

9. The method as defined in claim 5, further comprising inducing said eukaryotic promoter-driven RNA transcription by contacting a chemical agent containing 3-morpholino-propane-1-sulfonic acid (MOPS) with a transformed prokaryotic cell carrying at least a gene expression cassette encoding a sequence of SEQ.ID.NO.6, SEQ.ID.NO.7, SEQ.ID.NO.8, or SEQ.ID.NO.9, or a combination thereof.

10. The method as defined in claim 1, wherein said human lung cancer is lung adenocarcinoma.

11. The method as defined in claim 1, wherein said human lung cancer is non-small-cell lung cancer (NSCLC).

12. The method as defined in claim 1, wherein said pre-miRNA is used as a part of drug ingredients for pharmaceutical and therapeutic applications.

13. The method as defined in claim 1, wherein said pre-miRNA is useful for treating human lung cancer in vivo.

14. The method as defined in claim 13, wherein the treatment of said pre-miRNA inhibits cancer cell growth.

15. The method as defined in claim 13, wherein the treatment of said pre-miRNA suppresses the colony and nodule formation of cancer cells.

16. The method as defined in claim 13, wherein the treatment of said pre-miRNA inhibits cancer metastasis.

17. The method as defined in claim 13, wherein the treatment of said pre-miRNA prevents drug resistance of cancer cells.

18. The method as defined in claim 13, wherein the treatment of said pre-miRNA stimulates immune system responses against cancer cell growth.

19. The method as defined in claim 13, wherein the treatment of said pre-miRNA enhances normal tissue repairing in the cancer damaged tissue areas.

20. The method as defined in claim 1, wherein said anti-cancer effects include inhibition of lung cancer cell growth, suppression of cancer nodule formation, inhibition of cancer metastasis, prevention of drug resistance, increase of immune system responses, and enhancement of normal tissue repairing in the cancer damaged tissue areas.

* * * * *